United States Patent
Yokoyama et al.

(10) Patent No.: US 8,624,228 B2
(45) Date of Patent: Jan. 7, 2014

(54) COMPOUND HAVING PYRIDOINDOLE RING STRUCTURE BONDED WITH SUBSTITUTED PYRIDYL GROUP, AND ORGANIC ELECTROLUMINESCENT DEVICE

(75) Inventors: Norimasa Yokoyama, Tsukuba (JP); Shuichi Hayashi, Tsukuba (JP); Sawa Izumi, Tsukuba (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 172 days.

(21) Appl. No.: 12/867,556

(22) PCT Filed: Feb. 13, 2009

(86) PCT No.: PCT/JP2009/052408
§ 371 (c)(1),
(2), (4) Date: Aug. 13, 2010

(87) PCT Pub. No.: WO2009/102016
PCT Pub. Date: Aug. 20, 2009

(65) Prior Publication Data
US 2010/0308322 A1    Dec. 9, 2010

(30) Foreign Application Priority Data
Feb. 14, 2008  (JP) .................. 2008-032672

(51) Int. Cl.
*H01L 35/24* (2006.01)
*H01L 51/00* (2006.01)

(52) U.S. Cl.
USPC .................... 257/40; 257/E51.041

(58) Field of Classification Search
USPC ............................ 257/40, E51.041
See application file for complete search history.

(56) References Cited

U.S. PATENT DOCUMENTS

| | | | |
|---|---|---|---|
| 2006/0251918 A1* | 11/2006 | Iwakuma et al. | 428/690 |
| 2008/0014464 A1* | 1/2008 | Kawamura et al. | 428/690 |
| 2009/0045726 A1 | 2/2009 | Miki et al. | |
| 2011/0073852 A1* | 3/2011 | Yokoyama et al. | 257/40 |

FOREIGN PATENT DOCUMENTS

| | | |
|---|---|---|
| EP | 1 571 193 | 9/2005 |
| JP | 8 48656 | 2/1996 |
| JP | 2734341 | 1/1998 |

(Continued)

OTHER PUBLICATIONS

Hosokawa, C. et al.,"Japan Society of Applied Physics Ninth Workshop Preprint" pp. 55-61 (2001).*

(Continued)

*Primary Examiner* — Howard Weiss
(74) *Attorney, Agent, or Firm* — Oblon, Spivak, McClelland, Maier & Neustadt, L.L.P.

(57) ABSTRACT

Objects of the invention are to provide an organic compound having excellent properties, which is excellent in eleclron-injecting/transporling performance, has hole-blocking ability, and is highly stable in a thin-film state, as a material for an organic electroluminescent devices having a high-efficiency and a high durability; and to provide an organic electroluminescent device having a high-efficiency and a high durability using the compound. The invention relates to: a compound having a pyridoindolc ring structure bonded with a substituted pyridyl group and an organic electroluminescent device comprising a pair of electrodes and at least one organic layer interposed between the electrodes.

14 Claims, 4 Drawing Sheets

(56) References Cited

FOREIGN PATENT DOCUMENTS

| JP | 3194657 | 6/2001 |
|----|---------|--------|
| JP | 2006 156445 | 6/2006 |
| JP | 2007 080657 | 3/2007 |
| JP | 2007 180147 | 7/2007 |
| WO | 2004 053019 | 6/2004 |
| WO | 2008/020611 | 2/2008 |

OTHER PUBLICATIONS

"Optimization of Driving Lifetime Durability in Organic LED Devices Using Phosphorescent Guest emitter:Japan Society of AV Applied Physics Ninth Workshop Preprint", pp. 23-31 (2001).*

"Fiftieth Meeting of Japan Society of Applied Physics and Related Societies: 28P-A-6 Lecture Preprint", pp. 1412-1413 AW (2003).*

"Japan Society of Applied Physics", Journal of Organic Molecules/Bioelectronics Section, vol. 11, No. I, pp. 13-19 (2000).*

Derwent abstract of JP 2007-180147 (2007).*

Iwaki T. et al., "Novel Synthetic Strategy of Carbolines Via Palladium-Catalyzed Amination and Arylation Reaction", J. Chem. Soc., Perkin Tras. 1, pp. 1505-1511 (1999).

Kroehnke, F. "The Specific Synthesis of Pyridines and Oligopyridines", Synthesis, Supplement vol. IV, pp. 1-25 (Jan. 1976).

U.S. Appl. No. 12/865,736, filed Aug. 2, 2010, Yokoyama, et al.

U.S. Appl. No. 13/419,849, filed Mar. 14, 2012, Yokoyama, et al.

Supplemental European Search Report issued May 15, 2012 in connection with corresponding European Application No. 09 71 1282, filed Feb. 13, 2009.

* cited by examiner

COMPOUND HAVING PYRIDOINDOLE RING STRUCTURE BONDED WITH SUBSTITUTED PYRIDYL GROUP, AND ORGANIC ELECTROLUMINESCENT DEVICE

TECHNICAL FIELD

The present invention relates to a compound suitable for an organic electroluminescent (EL) device which is a self-luminescent device suitable for various displaying devices and a device. More specifically, it relates to a compound having a pyridoindole ring structure bonded with a substituted pyridyl group and to an organic EL device using the compound.

BACKGROUND ART

Since organic EL devices are self-luminescent devices, they are bright and excellent in visibility as compared with liquid-crystalline devices and capable of giving clear display, so that the organic EL devices have been actively studied.

In 1987, C. W. Tang et al. of Eastman Kodak Company put an organic EL device using organic materials into practical use by developing a device having a multilayered structure wherein various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1000 cd/m$^2$ or more at a voltage of 10 V or lower (see e.g., Patent Documents 1 and 2).

Patent Document 1: JP-A-8-48656
Patent Document 2: Japanese Patent No. 3194657

To date, many improvements have been performed for practical utilization of the organic EL devices, and high efficiency and durability have been achieved by an electroluminescent device wherein an anode, a hole-injecting layer, a hole-transporting layer, an emitting layer, an electron-transporting layer, an electron-injecting layer, and a cathode are sequentially provided on a substrate, to further segmentalize various roles (see e.g., Non-Patent Document 1).

Non-Patent Document 1: Japan Society of Applied Physics Ninth Workshop Preprint, pp. 55-61 (2001)

Moreover, for the purpose of further improvement of luminous efficiency, utilization of triplet exciton has been attempted and utilization of a phosphorescent material has been investigated (see e.g., Non-Patent Document 2).

Non-Patent Document 2: Japan Society of Applied Physics Ninth Workshop Preprint, pp. 23-31 (2001)

The emitting layer can be also prepared by doping a charge-transporting compound, generally called a host material, with a fluorescent material or a phosphorescent material. As described in the above-mentioned Workshop Preprints, the choice of the organic materials in organic EL devices remarkably affects various properties such as efficiency and durability of the devices.

In the organic EL devices, the charges injected from the both electrode are recombined in the emitting layer to attain light emission. However, since the mobility of holes is higher than the mobility of electrons, a problem of reduction in efficiency caused by a part of the holes passing through the emitting layer arises. Therefore, it is required to develop an electron-transporting material in which the mobility of electrons is high.

A representative light-emitting material, tris(8-hydroxyquinoline)aluminum (hereinafter referred to as Alq$_3$) is commonly used also as an electron-transporting material. However, since it has a work function of 5.8 eV, it cannot be considered that the material has hole-blocking capability.

As a technique to prevent the passing of a part of holes through the emitting layer and to improve probability of charge recombination in the emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (BAlq) (see e.g., Non-Patent Document 2), and the like.

On the other hand, as an electron-transporting material excellent in hole-blocking ability, there is proposed 3-(4-biphenylyl)-4-phenyl-5-(4-t-butylphenyl)-1,2,4-triazole (hereinafter referred to as TAZ) (see e.g., Patent Document 3).

Patent Document 3: Japanese Patent No. 2734341

Since TAZ has a work function as large as 6.6 eV and thus exhibits a high hole-blocking ability, it is used as an electron-transporting hole-blocking layer to be laminated onto the cathode side of a fluorescence-emitting layer or phosphorescence-emitting layer prepared by vacuum deposition, coating or the like, and contributes to increase the efficiency of organic EL devices (see e.g., Non-Patent Document 3).

Non-Patent Document 3: Fiftieth Meeting of Japan Society of Applied Physics and Related Societies, 28p-A-6 Lecture Preprint, p. 1413 (2003)

However, TAZ has a great problem of having low electron transport property, and it is necessary to prepare an organic electroluminescent device in combination with an electron-transporting material having a higher electron transport property (see e.g., Non-Patent Document 4).

Non-Patent Document 4: Japan Society of Applied Physics, Journal of Organic Molecules/Bioelectronics Section, Vol. 11, No. 1, pp. 13-19 (2000)

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in thin-film stability or are insufficient in the function of blocking holes. In order to improve characteristic properties of the organic electroluminescent devices, it is desired to develop an organic compound which is excellent in electron-injection/transport performances and hole-blocking ability and is highly stable in a thin-film state.

DISCLOSURE OF THE INVENTION

Problems to be Solved by the Invention

Objects of the present invention are to provide an organic compound having excellent properties, which is excellent in electron-injection/transport performances, has hole-blocking ability and is highly stable in a thin-film state, as a material for an organic electroluminescent device having a high efficiency and a high durability, and to provide an organic electroluminescent device having a high efficiency and a high durability using the compound.

As physical properties of the organic compound to be provided by the invention, there may be mentioned (1) a good electron injection characteristic, (2) a high electron mobility, (3) an excellent hole-blocking ability, (4) good stability in a thin-film state, and (5) excellent thermal resistance. In addition, as physical properties of the organic electroluminescent device to be provided by the invention, there may be mentioned (1) high luminous efficiency, (2) low emission initiation voltage, (3) low practical driving voltage.

Means for Solving the Problems

Thus, in order to achieve the above objects, the present inventors have designed and chemically synthesized compounds having a pyridoindole ring structure bonded with a substituted pyridyl group, with focusing on the fact that the nitrogen atom of the pyridine ring which exhibits affinity to an electron has an ability of coordinating to a metal and is excellent in thermal resistance. The present inventors have experimentally produced various organic EL devices using the compounds, and have extensively performed property evaluation of the devices. As a result, they have accomplished the invention.

That is, the invention provides: a compound having a pyridoindole ring structure bonded with a substituted pyridyl group and is represented by the following general formula (1); and an organic electroluminescent device comprising a pair of electrodes and at least one organic layer interposed between the electrodes, wherein the at least one organic layer contains the compound:

[Chem. 1]

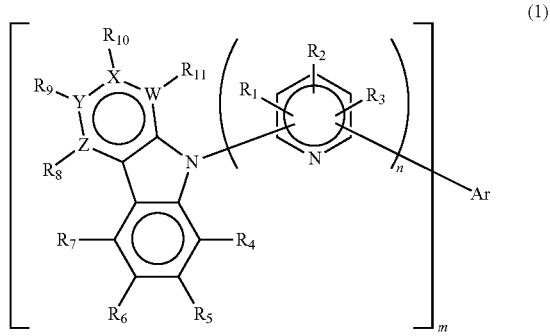

wherein Ar represents a substituted or unsubstituted aromatic hydrocarbon group, a substituted or unsubstituted aromatic heterocyclic group, or a substituted or unsubstituted condensed polycyclic aromatic group; $R_1$ to $R_3$ may be the same or different and represent a hydrogen atom, a substituted or unsubstituted aromatic heterocyclic group, or a substituted or unsubstituted condensed polycyclic aromatic group; $R_4$ to $R_{11}$ may be the same or different and represent a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, a substituted or unsubstituted aromatic heterocyclic group, or a substituted or unsubstituted condensed polycyclic aromatic group; m and n represent an integer of 1 to 3; and W, X, Y, and Z represent a carbon atom or a nitrogen atom, provided that the case where $R_1$ to $R_3$ in the molecule are simultaneously all hydrogen atoms is excluded, and that only one of W, X, Y, and Z is a nitrogen atom and the nitrogen atom does not have the substituent $R_8$, $R_9$, $R_{10}$, or $R_{11}$.

Of the compounds represented by general formula (1), compounds in which n=1 are preferred. Alternatively, compounds in which m=1 and either n=2 or n=3 are preferred.

The "aromatic hydrocarbon group", the "aromatic heterocyclic group" or the "condensed polycyclic aromatic group" in the substituted or unsubstituted aromatic hydrocarbon group, the substituted or unsubstituted aromatic heterocyclic group, or the substituted or unsubstituted condensed polycyclic aromatic group, which is represented by Ar in the general formula (1), specifically includes a phenyl group, a biphenyl group, a terphenyl group, a tetrakisphenyl group, a styryl group, a naphthyl group, an anthryl group, an acenaphthenyl group, a fluorenyl group, a phenanthryl group, an indenyl group, a pyrenyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group, and an acridinyl group.

The "substituent" in the substituted aromatic hydrocarbon group, the substituted aromatic heterocyclic group, or the substituted condensed polycyclic aromatic group, represented by Ar in the general formula (1), specifically includes groups such as a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

The "aromatic heterocyclic group" or the "condensed polycyclic aromatic group" in the substituted or unsubstituted aromatic heterocyclic group or the substituted or unsubstituted condensed polycyclic aromatic group, represented by $R_1$ to $R_3$ in the general formula (1), specifically includes a pyridyl group, a pyrimidyl group, a furanyl group, a pyrrolyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthridinyl group, a phenanthrolinyl group, and an acridinyl group.

The "aromatic hydrocarbon group", the "aromatic heterocyclic group", or the "condensed polycyclic aromatic group" in the substituted or unsubstituted aromatic hydrocarbon group, the substituted or unsubstituted aromatic heterocyclic group, or the substituted or unsubstituted condensed polycyclic aromatic group, represented by $R_4$ to $R_{11}$ in the general formula (1), specifically includes a phenyl group, a biphenyl group, a terphenyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyrrolyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthridinyl group, a phenanthrolinyl group, and an acridinyl group.

The "substituent" in the substituted aromatic heterocyclic group or the substituted condensed polycyclic aromatic group, represented by $R_1$ to $R_3$ in the general formula (1), specifically includes a fluorine atom, a chlorine atom, a trifluoromethyl group, linear or branched alkyl groups having 1-6 carbon atoms, a phenyl group, a biphenyl group, a terphenyl group, a tetrakisphenyl group, a styryl group, a naphthyl group, a fluorenyl group, a phenanthryl group, an indenyl group, and a pyrenyl group. These substituents may have been further substituted.

The "substituent" in the substituted aromatic hydrocarbon group, the substituted aromatic heterocyclic group, or the substituted condensed polycyclic aromatic group, represented by $R_4$ to $R_{11}$ in the general formula (1), specifically includes a fluorine atom, a chlorine atom, a trifluoromethyl group, linear or branched alkyl groups having 1-6 carbon atoms, a phenyl group, a biphenyl group, a terphenyl group, a tetrakisphenyl group, a styryl group, a naphthyl group, a fluorenyl group, a phenanthryl group, an indenyl group, and a pyrenyl group. These substituents may have been further substituted.

The compound having a pyridoindole ring structure bonded with a substituted pyridyl group, which is represented by the general formula (1) of the invention, is a novel compound, provides high electron mobility as compared with conventional electron-transporting materials, has an excellent hole-blocking ability, and is stable in a thin-film state.

The compound having a pyridoindole ring structure bonded with a substituted pyridyl group, which is represented by the general formula (1) of the invention, can be used as a constituent material for an electron-transporting layer of an organic electroluminescent device (hereinafter, abbreviated as organic EL device). The use of the material exhibiting a higher electron injection/mobile rate as compared with conventional materials provides effects of improving electron transport efficiency from the electron-transporting layer to an emitting layer to enhance luminous efficiency and also lowering a driving voltage to enhance durability of the organic EL device.

The compound having a pyridoindole ring structure bonded with a substituted pyridyl group, which is represented by the general formula (1) of the invention, can be also used as a constituent material for a hole-blocking layer of an organic EL device. The use of the material excellent in hole-blocking ability and also excellent in electron transport property as compared with conventional materials and having high stability in a thin-film state provides effects of lowering a driving voltage, improving current resistance, and enhancing maximum emission luminance of the organic EL device, while exhibiting a high luminous efficiency.

The compound having a pyridoindole ring structure bonded with a substituted pyridyl group, which is represented by the general formula (1) of the invention, can be also used as a constituent material for an emitting layer of an organic EL device. The use of an emitting layer prepared by using the material of the invention excellent in electron transport property as compared with conventional materials and having a wide band-gap as a host material for the emitting layer and making a fluorescent material or a phosphorescent material, called a dopant, carried thereon provides an effect of realizing an organic EL device exhibiting a lowered driving voltage and having an improved luminous efficiency.

The organic EL device of the invention uses the compound having a pyridoindole ring structure bonded with a substituted pyridyl group, which compound exhibits high electron mobility as compared with a conventional electron-transporting materials, has an excellent hole-blocking ability and is stable in a thin-film state. Therefore, it becomes possible to realize high efficiency and high durability.

Advantageous Effects of the Invention

The compound having a pyridoindole ring structure bonded with a substituted pyridyl group of the invention is useful as a constituent material for an electron-transporting layer, a hole-blocking layer, or an emitting layer of an organic EL device, and the compound exhibits an excellent hole-blocking ability, is stable in a thin-film state, and has excellent thermal resistance. The organic EL device of the invention exhibits a high luminous efficiency, whereby the practical driving voltage of the device can be lowered. By lowering the light emission initiation voltage, the durability can be improved.

DESCRIPTION OF REFERENCE NUMERALS AND SIGNS

Figure 1:
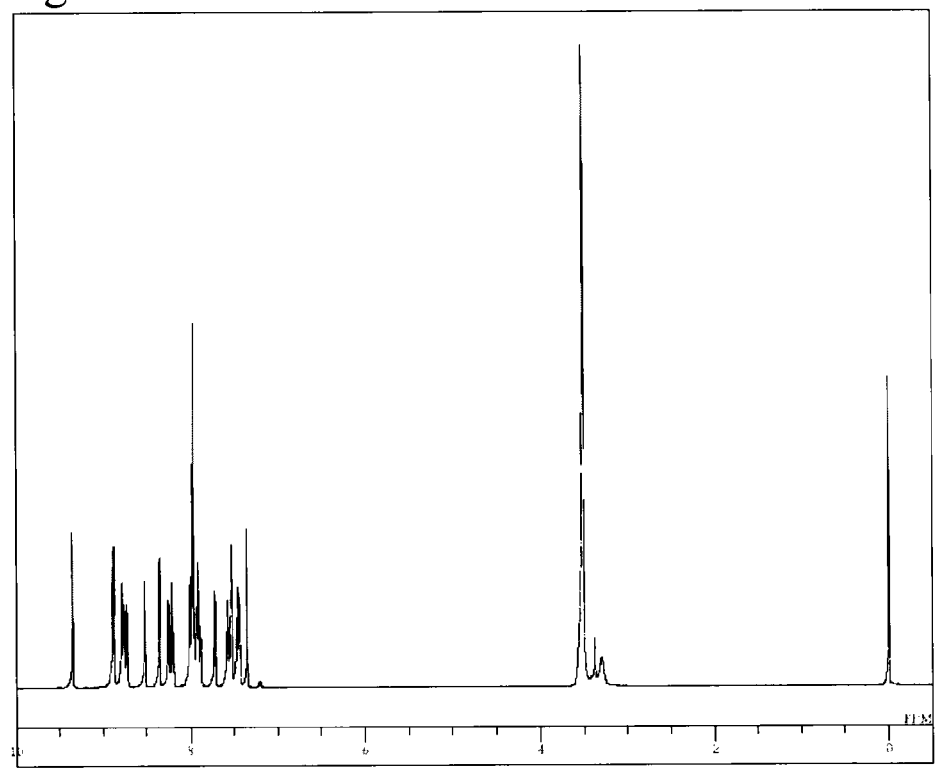
FIG. 1 is a $^1$H-NMR chart of the compound (Compound 27) of Invention Example 1.

1: Glass substrate
2: Transparent anode
3: Hole-injecting layer
4: Hole-transporting layer
5: Emitting layer
6: Hole-blocking layer
7: Electron-transporting layer
8: Electron-injecting layer
9: Cathode

BEST MODE FOR CARRYING OUT THE INVENTION

The compounds having a pyridoindole ring structure connected with a substituted pyridyl group of the invention are novel compounds, and these compounds can be synthesized, for example, by the following method. A compound having a pyridoindole ring structure bonded with a substituted pyridyl group can be synthesized by first subjecting a corresponding halogenoanilinopyridine to a cyclization reaction by a palladium catalyst to synthesize a pyridoindole ring (see, e.g., Non-Patent Document 5) and then condensing it with various halogenopyridines having a pyridyl group. The various halogenopyridines having a pyridyl group can be synthesized by condensing corresponding an aldehyde with an acetylpyridine in the presence of a base and further subjecting the condensates to a reaction with a corresponding pyridinium iodide (see, e.g., Non-Patent Document 6).

Non-Patent Document 5: J. Chem. Soc., Perkin Trans. 1, p. 1505 (1999)

Non-Patent Document 6: Synthesis, 1 (1976)

Among the compounds having a pyridoindole ring structure bonded with a substituted pyridyl group, which is represented by the general formula (1), specific examples of preferred compounds are shown below, but the invention is not limited to these compounds.

[Chem. 2]
(Compound 2)
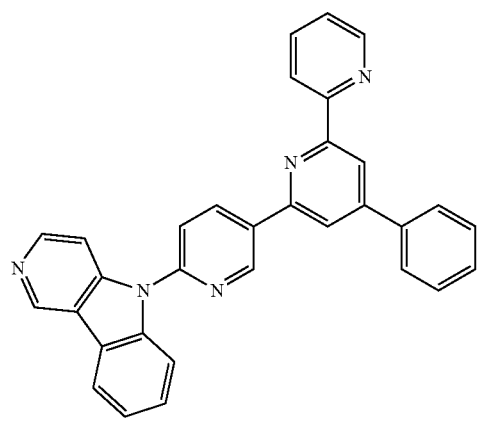
[Chem. 3]
(Compound 3)
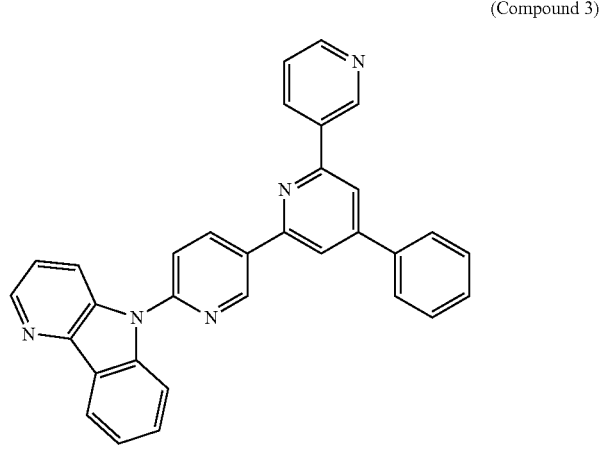
[Chem. 4]
(Compound 4)
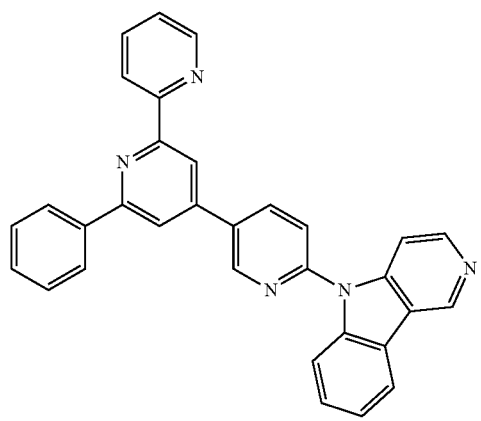
[Chem. 5]
(Compound 5)
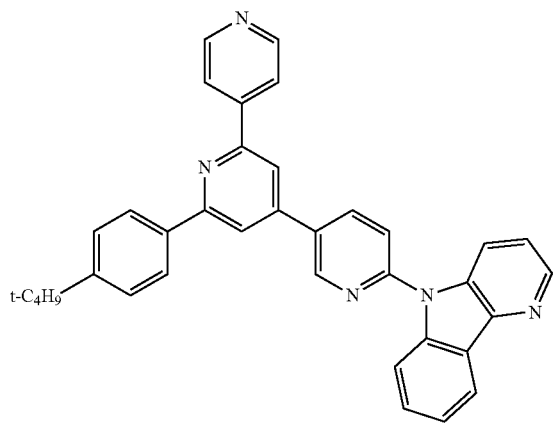
[Chem. 6]
(Compound 6)
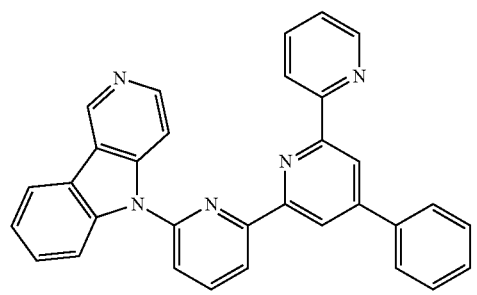
[Chem. 7]
(Compound 7)
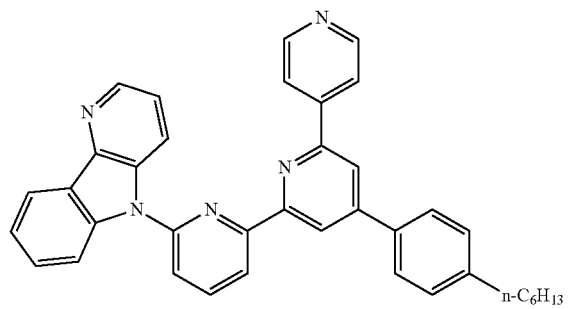

-continued
[Chem. 8]
(Compound 8)
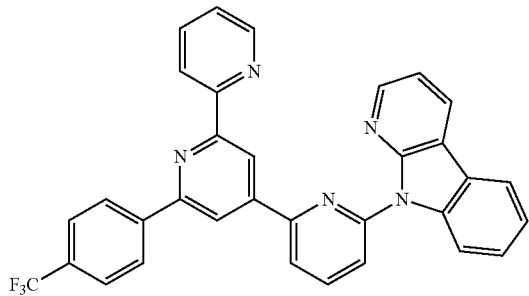
[Chem. 9]
(Compound 9)
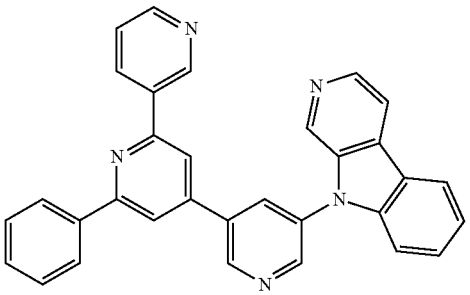
[Chem. 10]
(Compound 10)
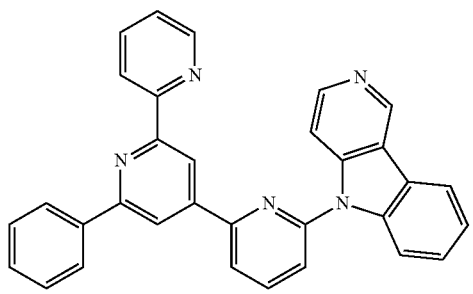
[Chem. 11]
(Compound 11)
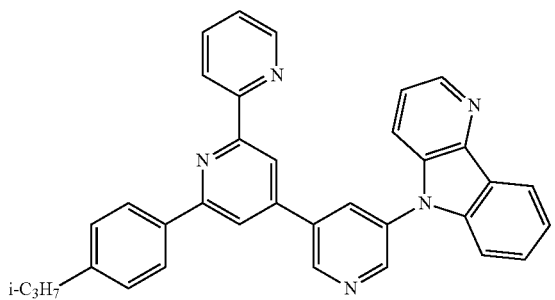
[Chem. 12]
(Compound 12)
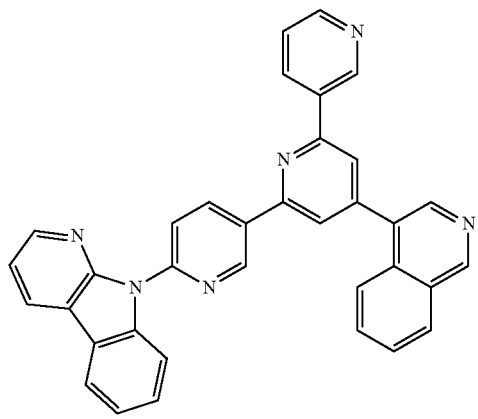
[Chem. 13]
(Compound 13)
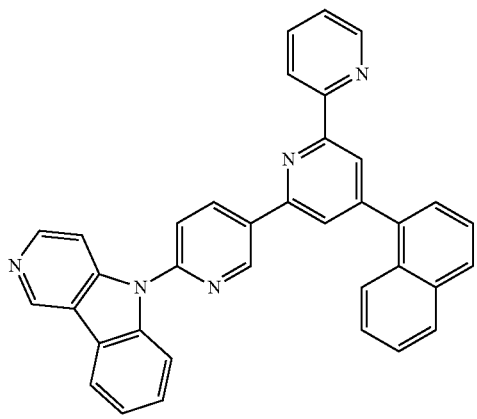

-continued
(Compound 14)
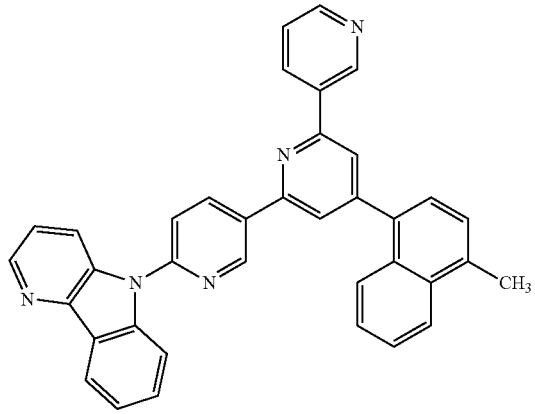
(Compound 15)
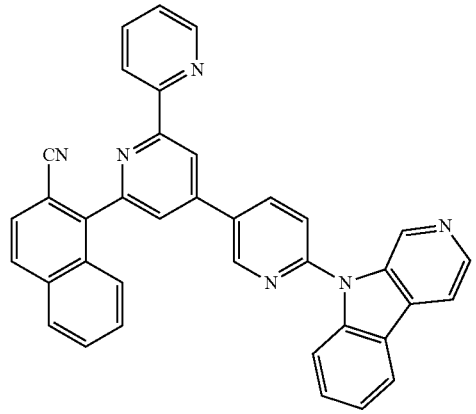
(Compound 16)
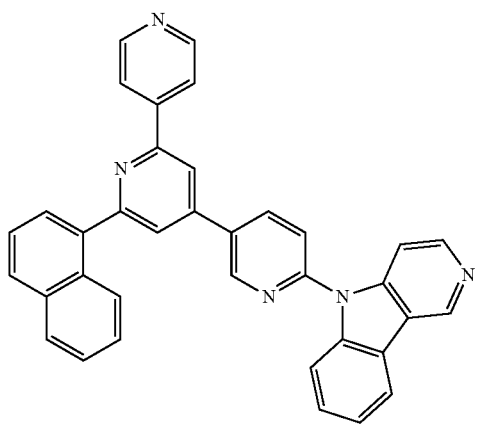
(Compound 17)
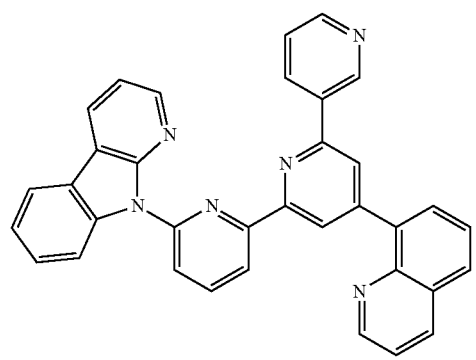
(Compound 18)
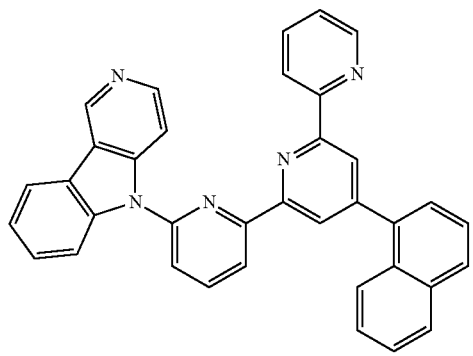
(Compound 19)
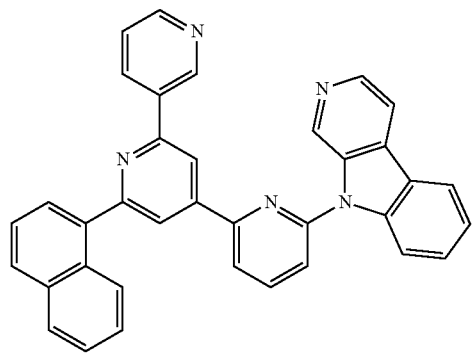

-continued
[Chem. 20]
(Compound 20)
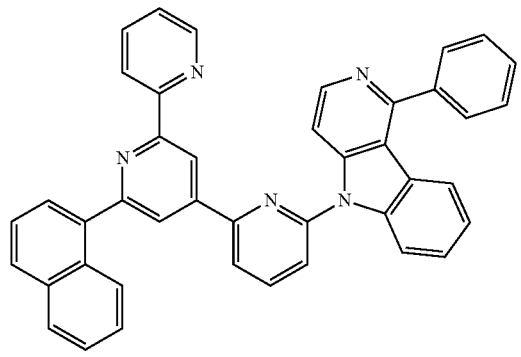
[Chem. 21]
(Compound 21)
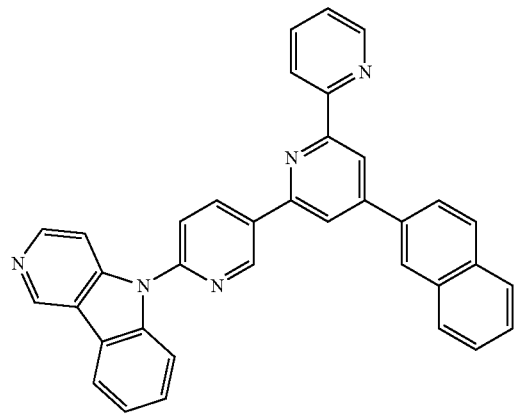
[Chem. 22]
(Compound 22)
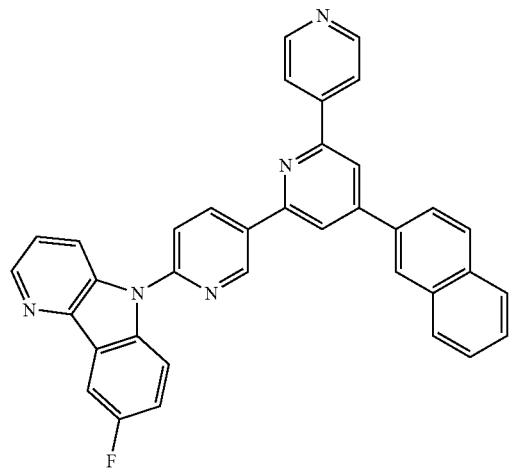
[Chem. 23]
(Compound 23)
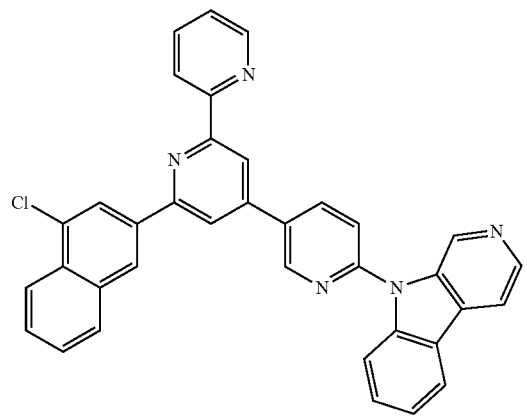
[Chem. 24]
(Compound 24)
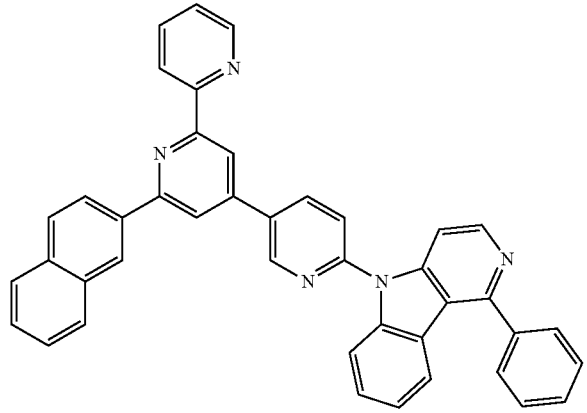
[Chem. 25]
(Compound 25)
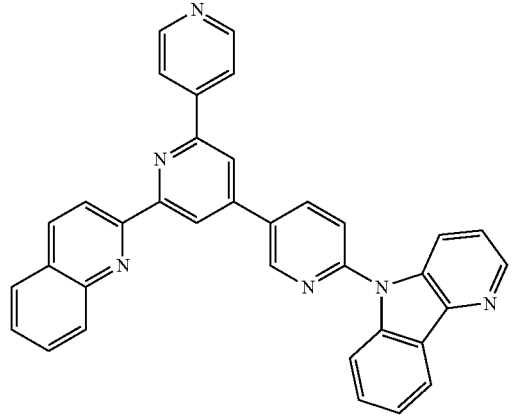

-continued
[Chem. 26]
(Compound 26)
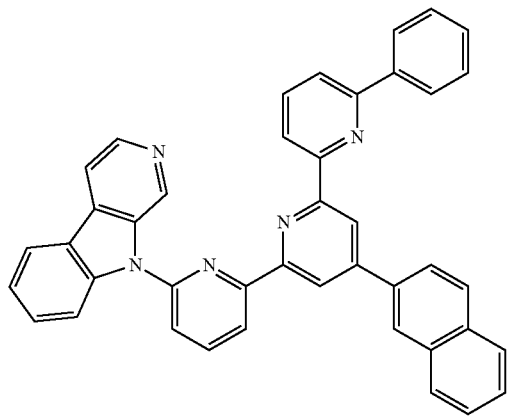
[Chem. 27]
(Compound 27)
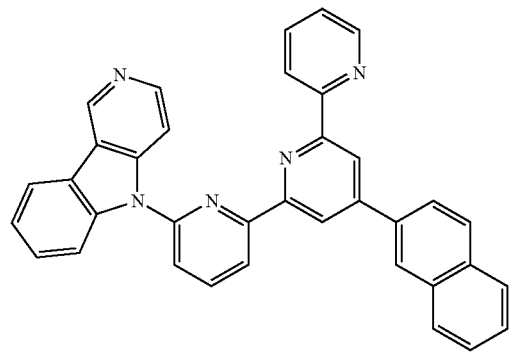
[Chem. 28]
(Compound 28)
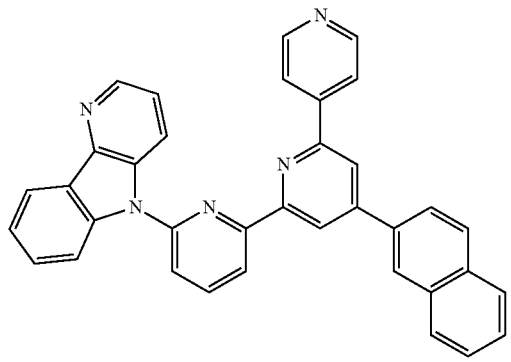
[Chem. 29]
(Compound 29)
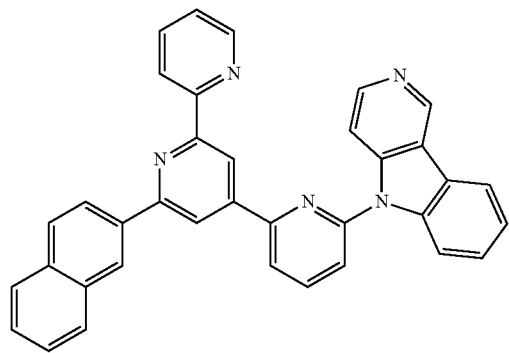
[Chem. 30]
(Compound 30)
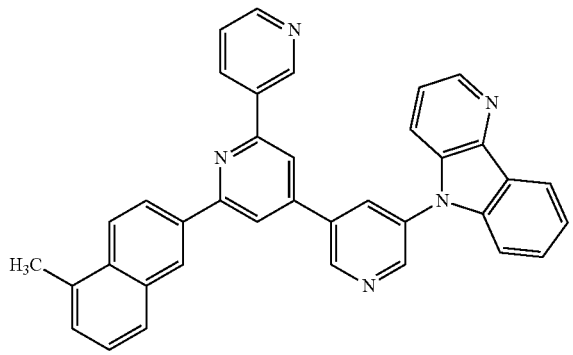
[Chem. 31]
(Compound 31)
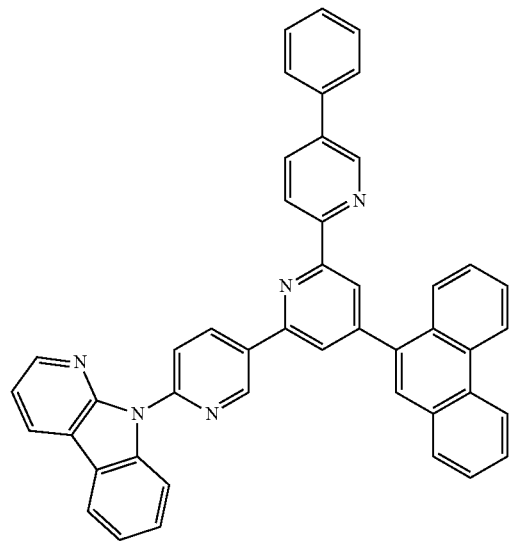

-continued
[Chem. 32]
(Compound 32)
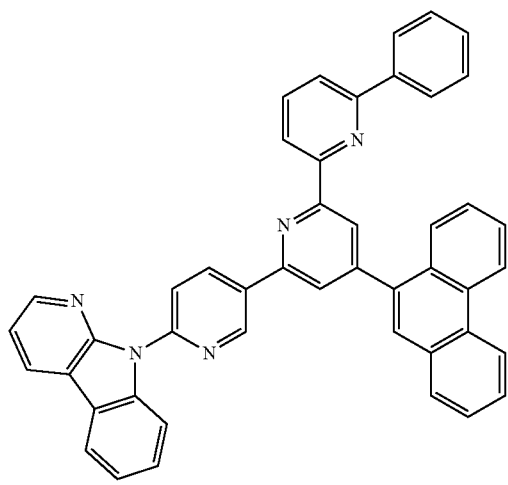
[Chem. 33]
(Compound 33)
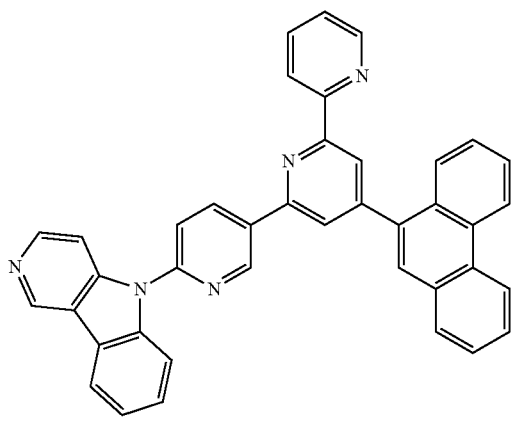
[Chem. 34]
(Compound 34)
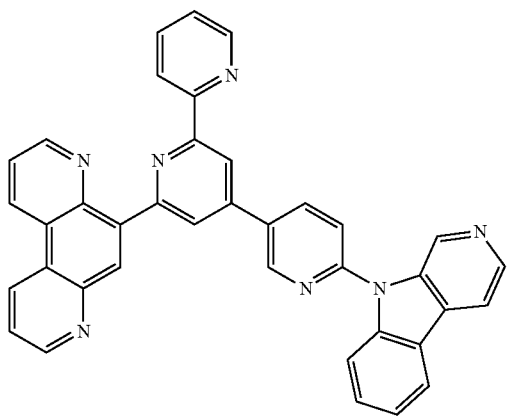
[Chem. 35]
(Compound 35)
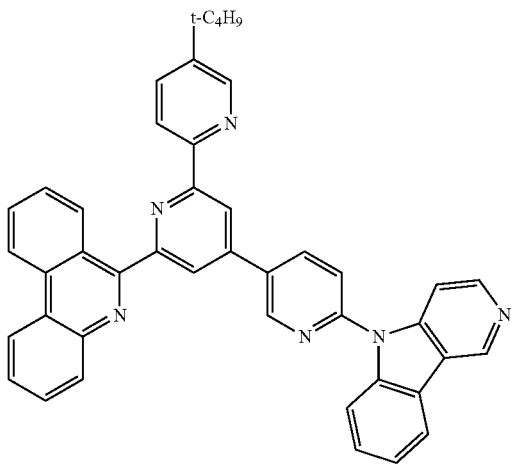
[Chem. 36]
(Compound 36)
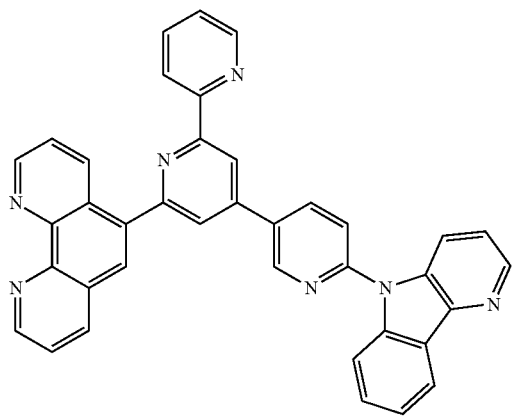
[Chem. 37]
(Compound 37)
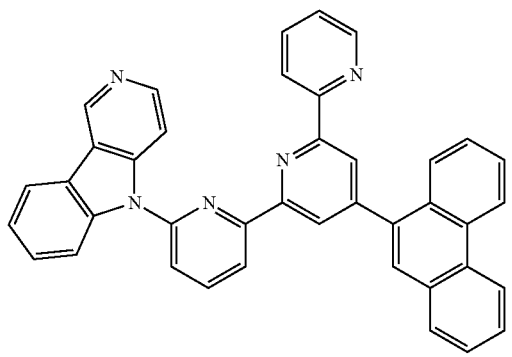

[Chem. 38]
(Compound 38)
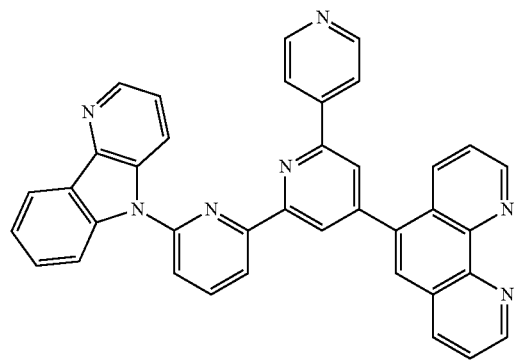
[Chem. 39]
(Compound 39)
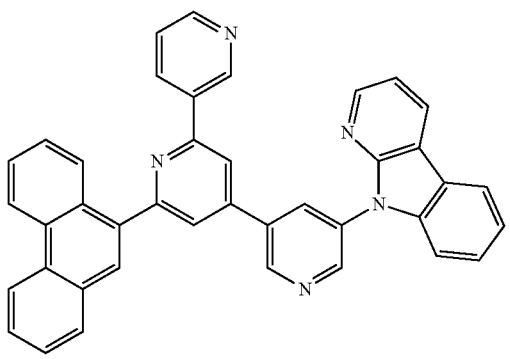
[Chem. 40]
(Compound 40)
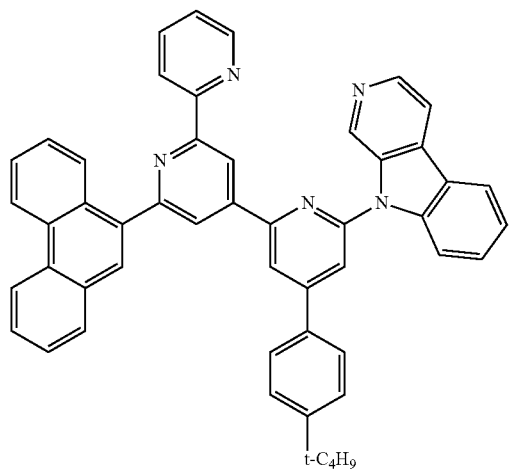
[Chem. 41]
(Compound 41)
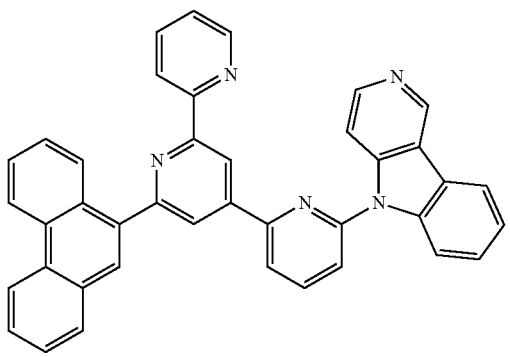
[Chem. 42]
(Compound 42)
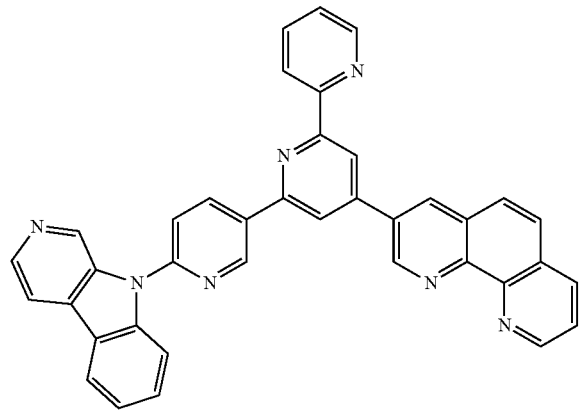
[Chem. 43]
(Compound 43)
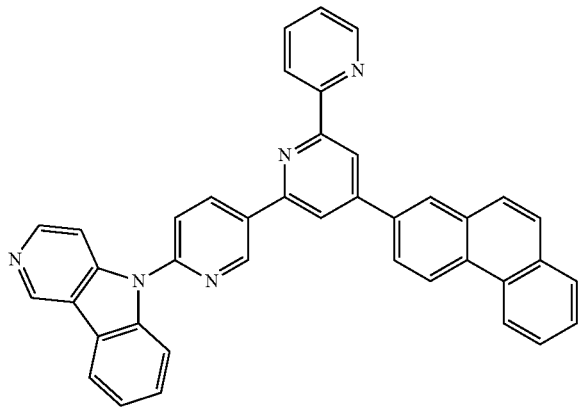

-continued
[Chem. 44]
(Compound 44)
[Chem. 45]
(Compound 45)
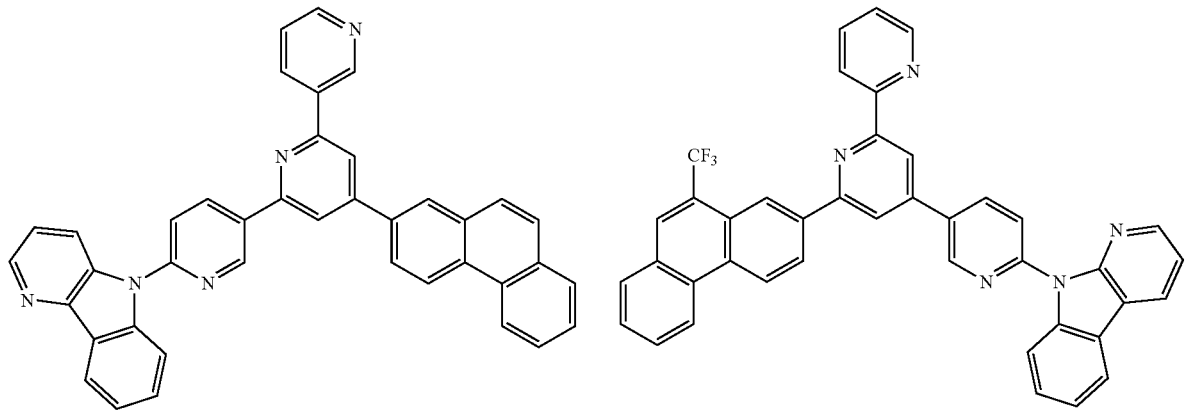
[Chem. 46]
(Compound 46)
[Chem. 47]
(Compound 47)
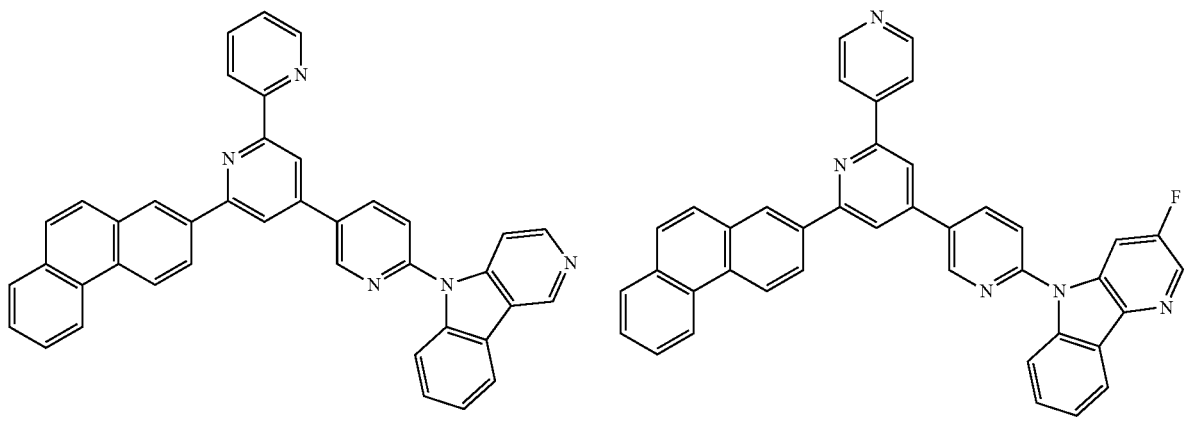
[Chem. 48]
(Compound 48)
[Chem. 49]
(Compound 49)
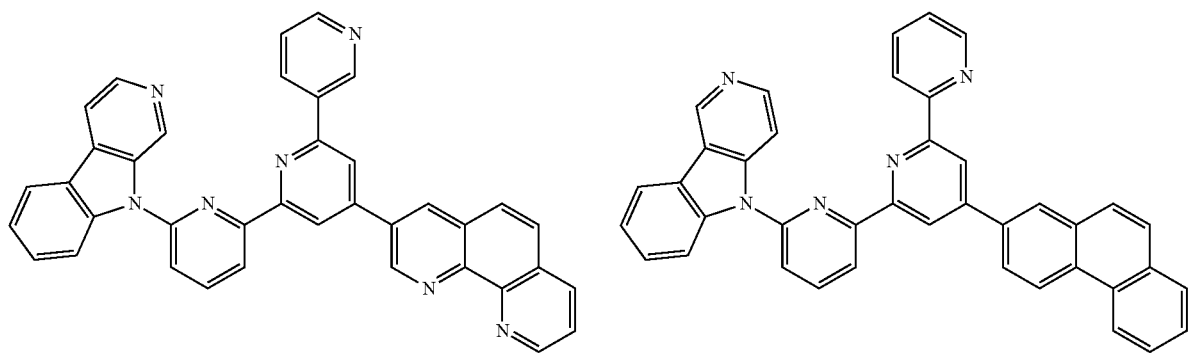

-continued
(Compound 50)
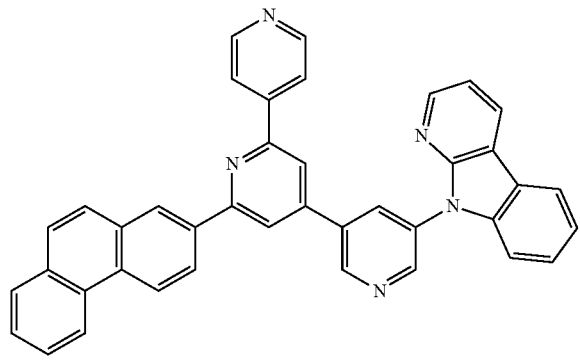
(Compound 51)
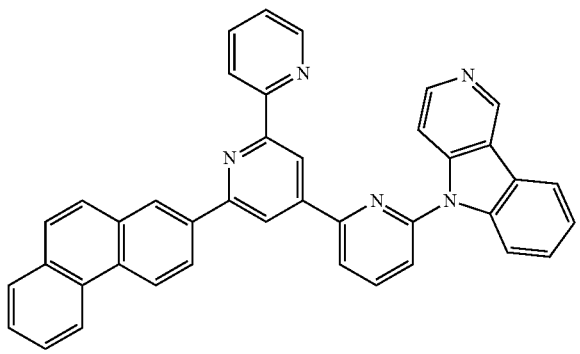
(Compound 52)
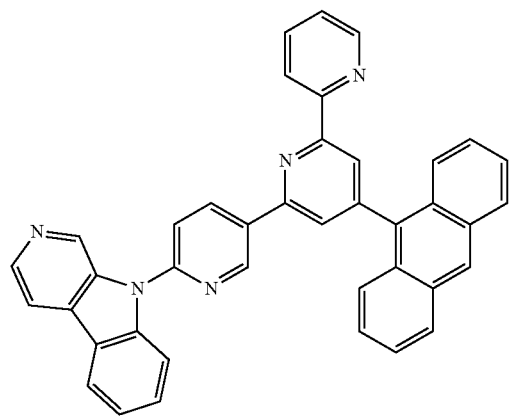
(Compound 53)
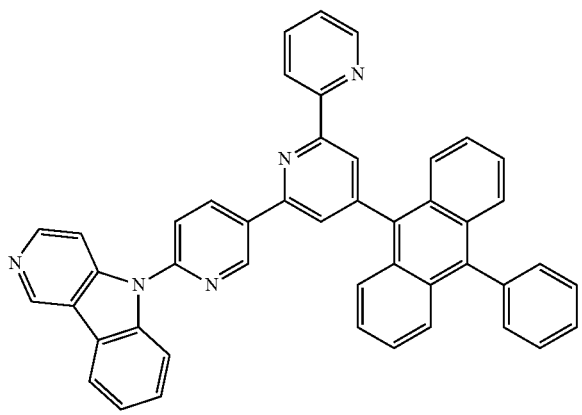
(Compound 54)
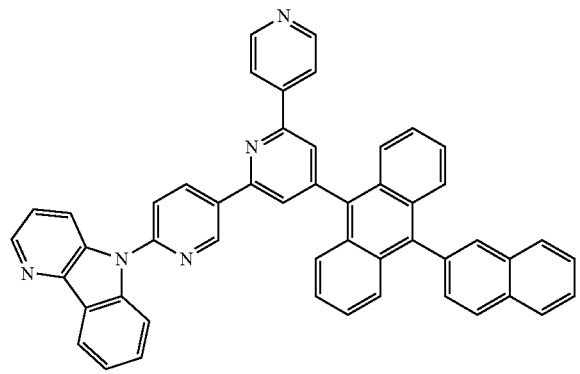
(Compound 55)
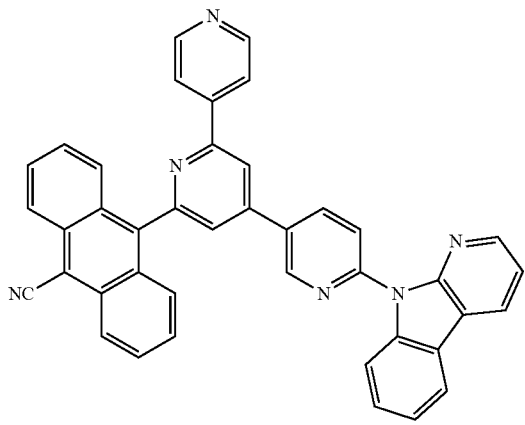

-continued
[Chem. 56]
(Compound 56)
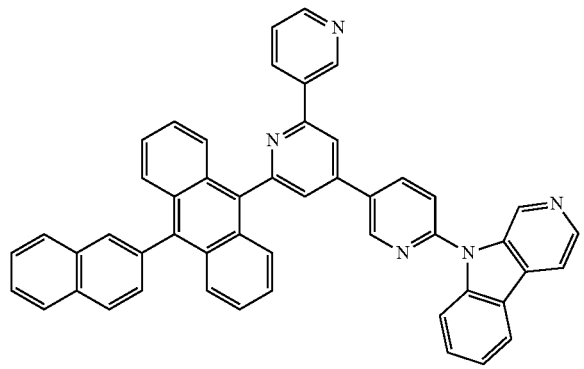
[Chem. 57]
(Compound 57)
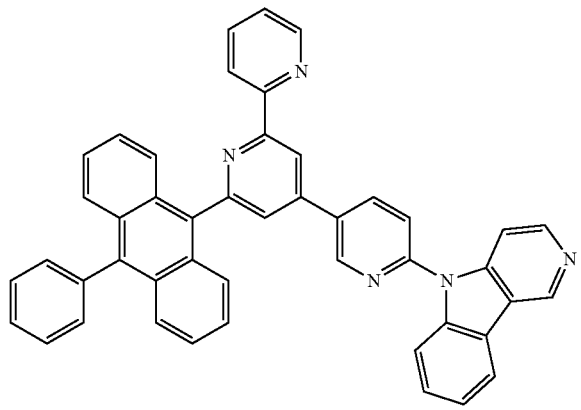
[Chem. 58]
(Compound 58)
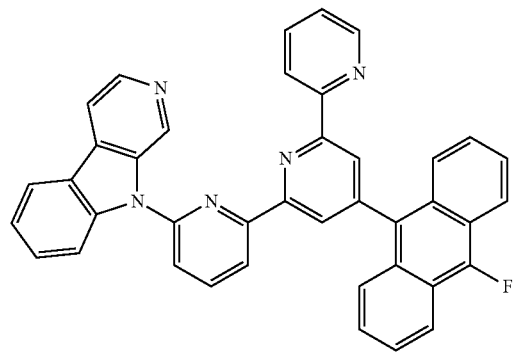
[Chem. 59]
(Compound 59)
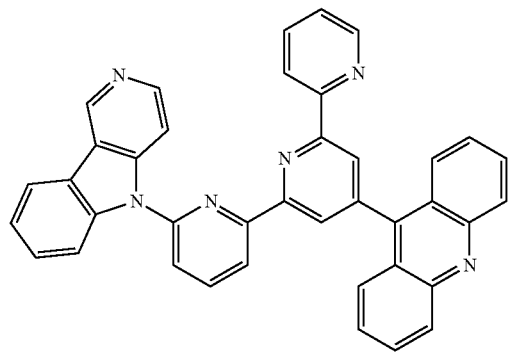
[Chem. 60]
(Compound 60)
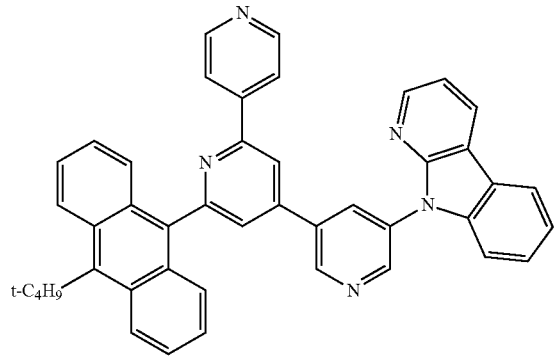
[Chem. 61]
(Compound 61)
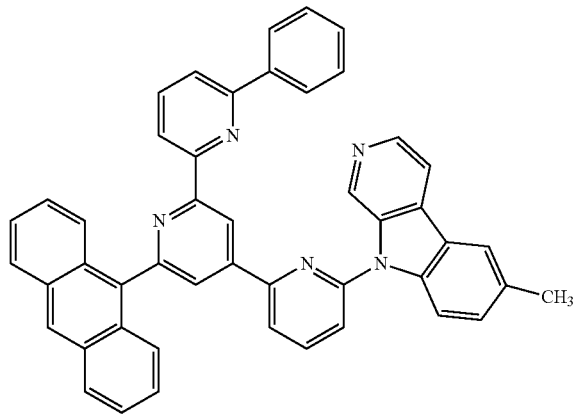

-continued
[Chem. 62]
(Compound 62)
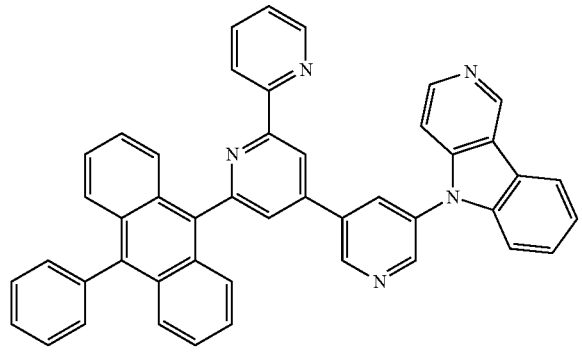
[Chem. 63]
(Compound 63)
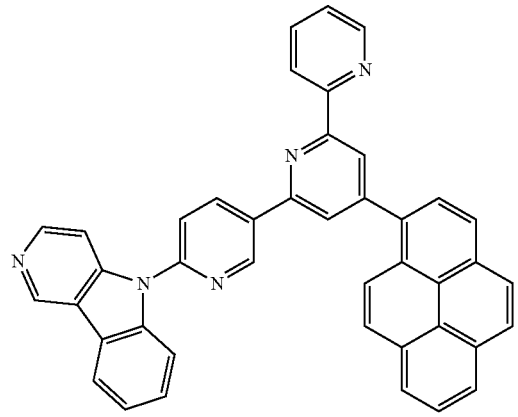
[Chem. 64]
(Compound 64)
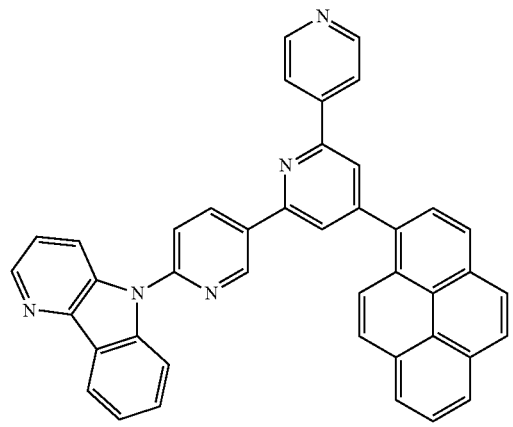
[Chem. 65]
(Compound 65)
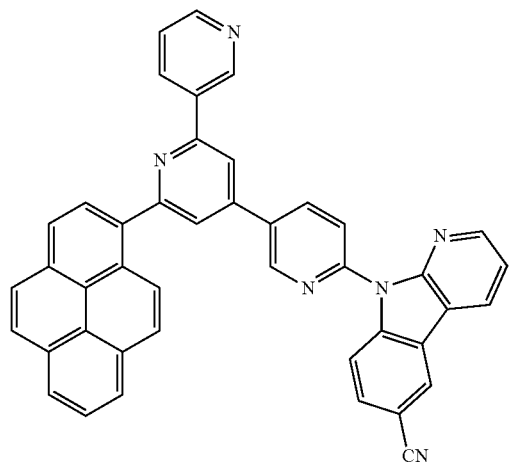
[Chem. 66]
(Compound 66)
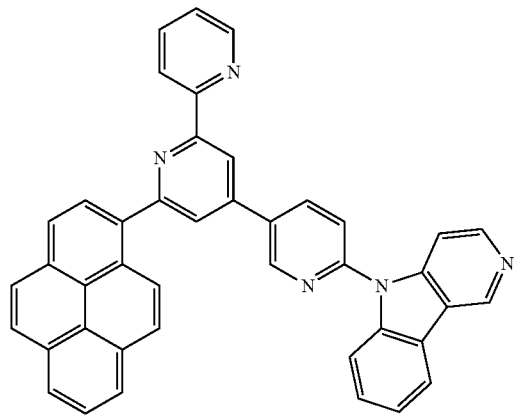
[Chem. 67]
(Compound 67)
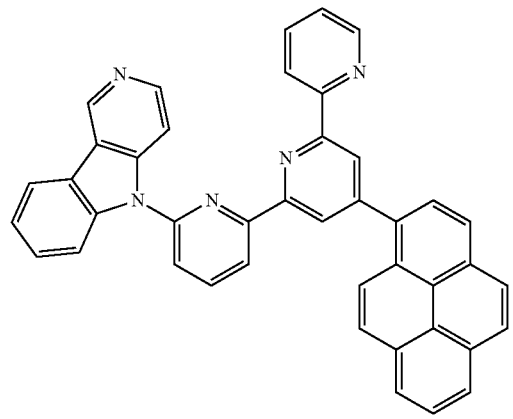

-continued
[Chem. 68]
(Compound 68)
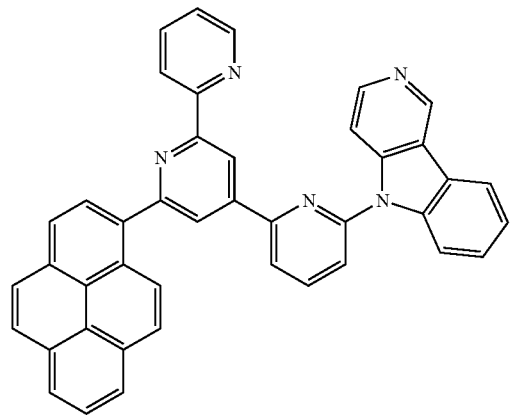
[Chem. 69]
(Compound 69)
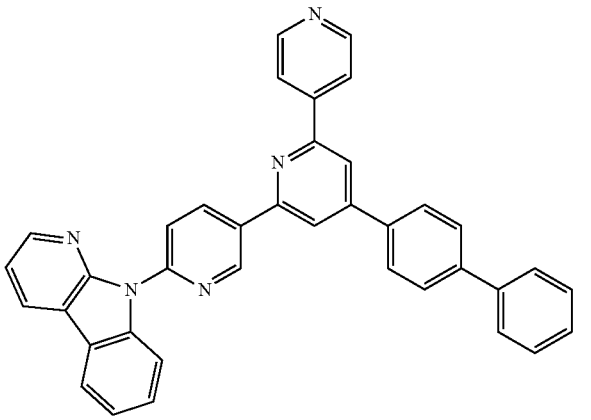
[Chem. 70]
(Compound 70)
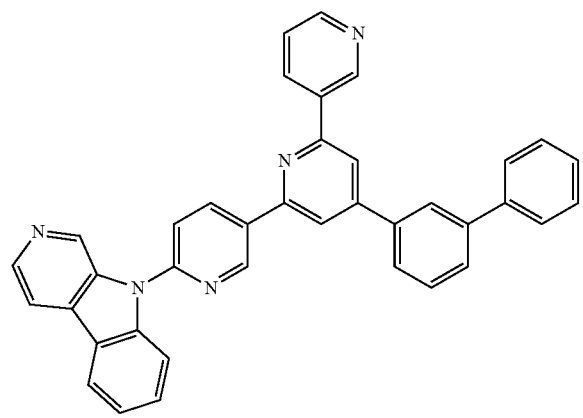
[Chem. 71]
(Compound 71)
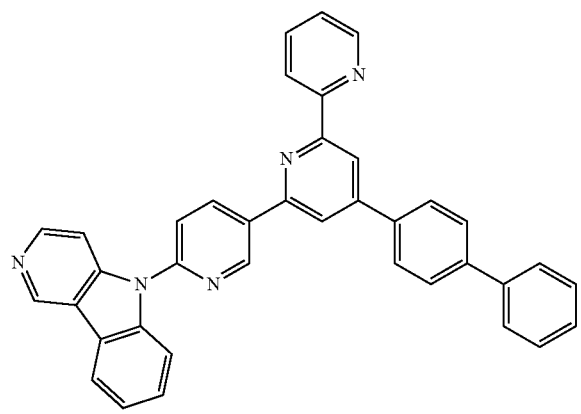
[Chem. 72]
(Compound 72)
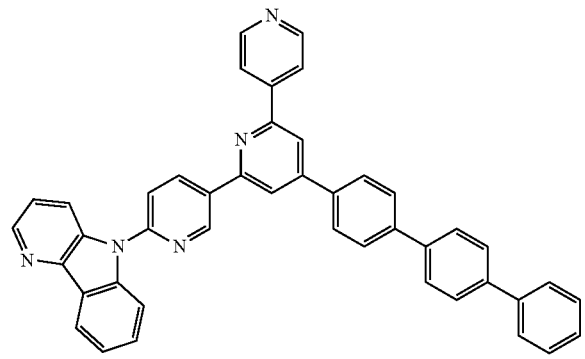
[Chem. 73]
(Compound 73)
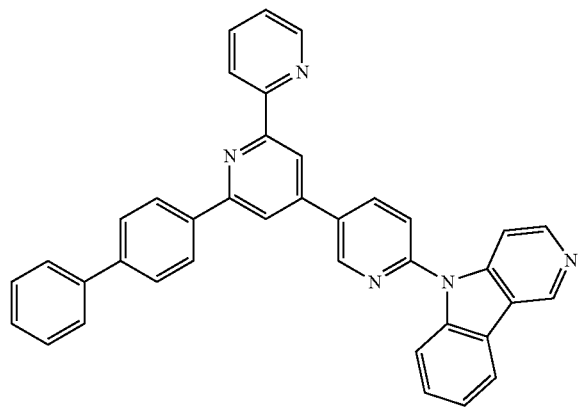

-continued
[Chem. 74]
(Compound 74)
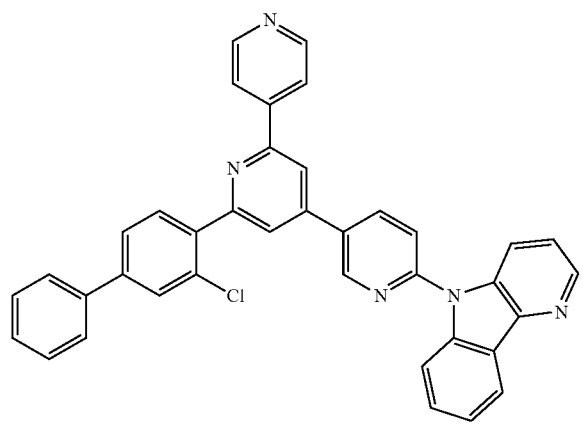
[Chem. 75]
(Compound 75)
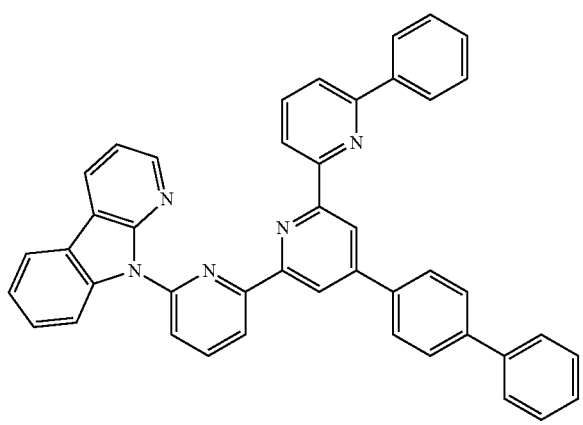
[Chem. 76]
(Compound 76)
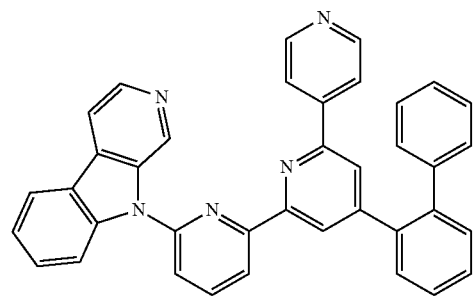
[Chem. 77]
(Compound 77)
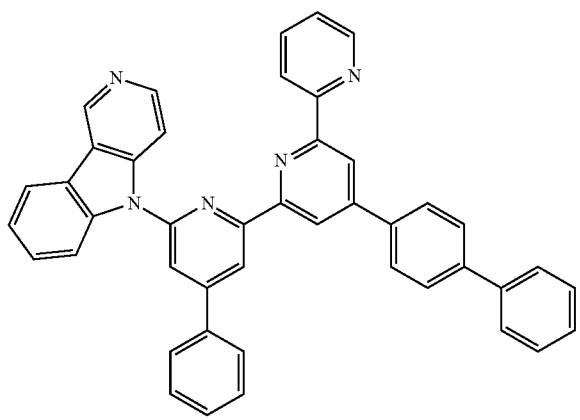
[Chem. 78]
(Compound 78)
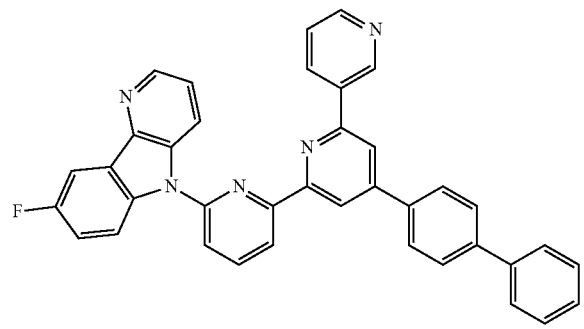
[Chem. 79]
(Compound 79)
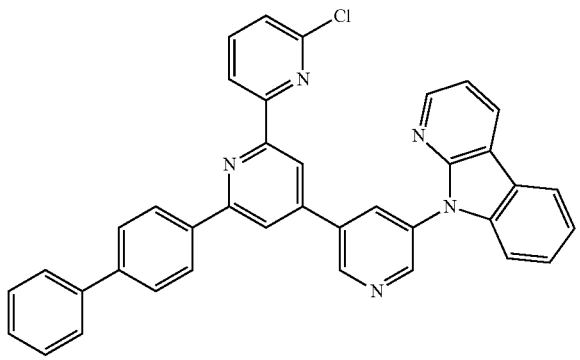

-continued
(Compound 80)
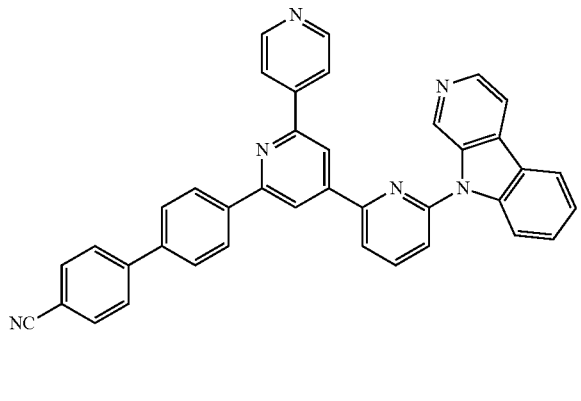
(Compound 81)
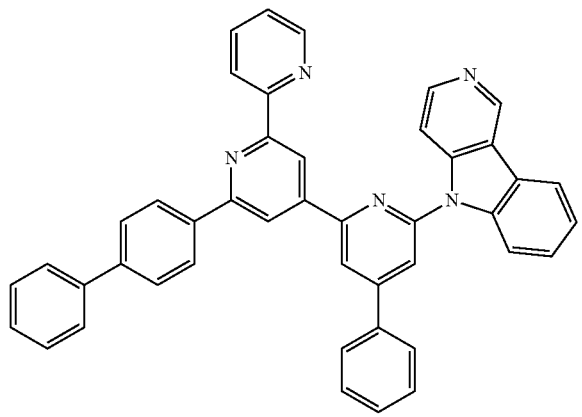
(Compound 82)
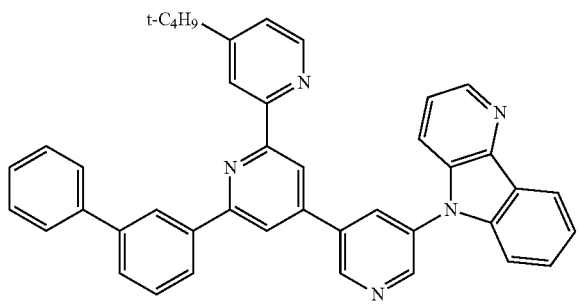
(Compound 83)
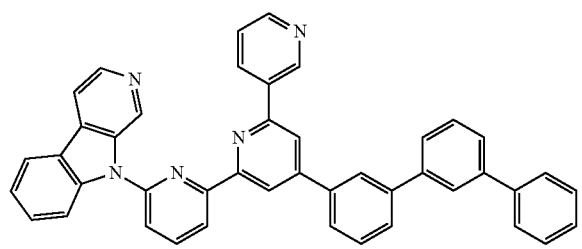
(Compound 84)
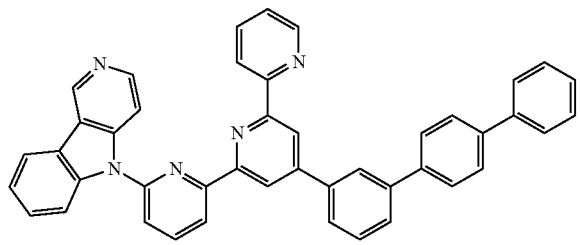
(Compound 85)
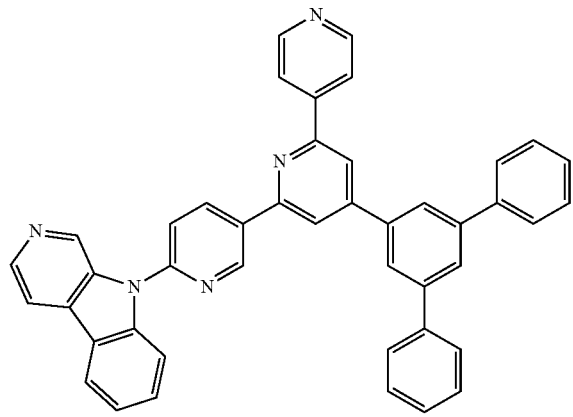

-continued
[Chem. 86]
(Compound 86)
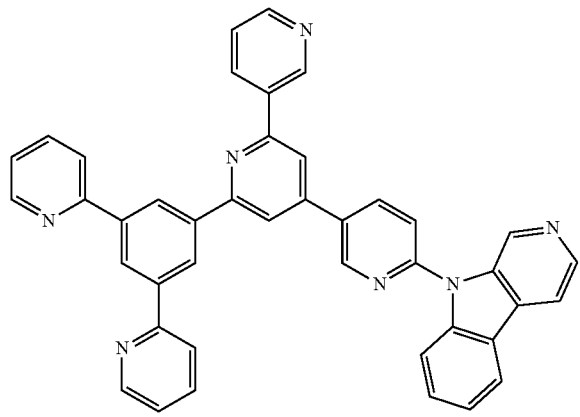
[Chem. 87]
(Compound 87)
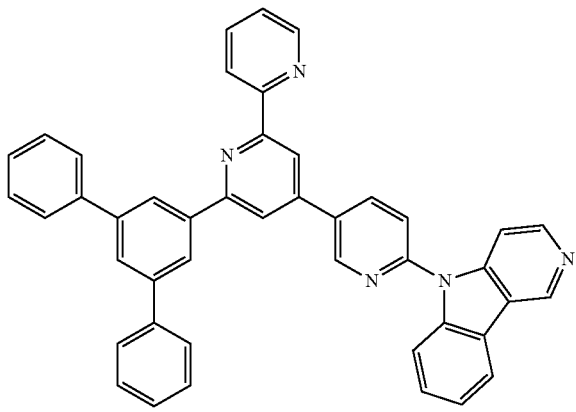
[Chem. 88]
(Compound 88)
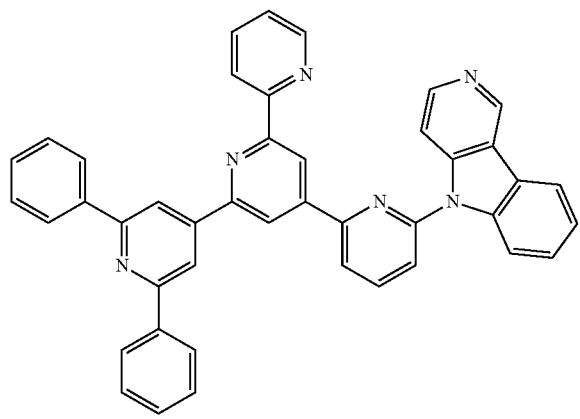
[Chem. 89]
(Compound 89)
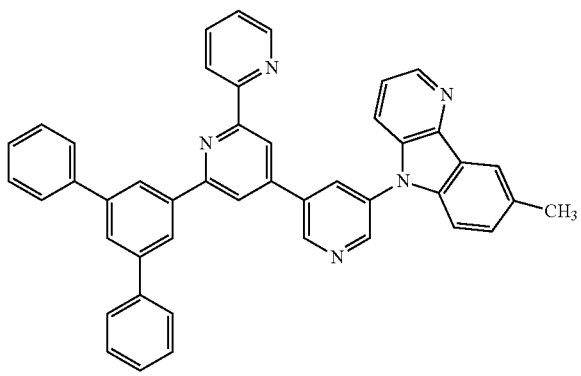
[Chem. 90]
(Compound 90)
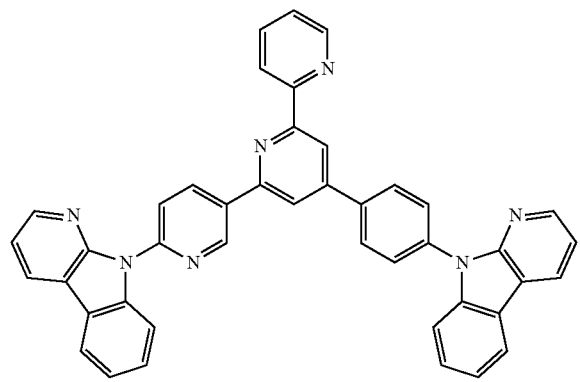
[Chem. 91]
(Compound 91)
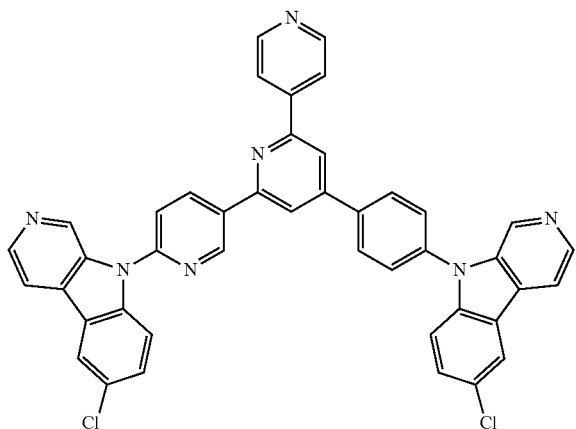

-continued
[Chem. 92]
(Compound 92)
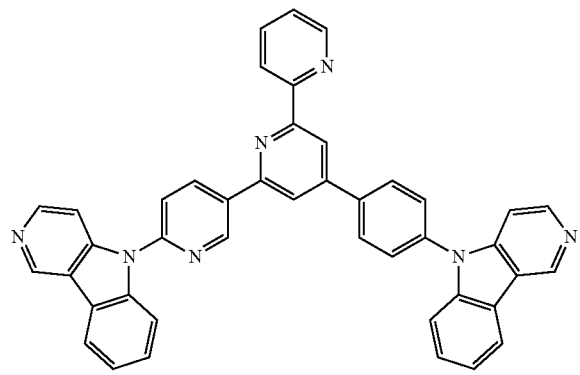
[Chem. 93]
(Compound 93)
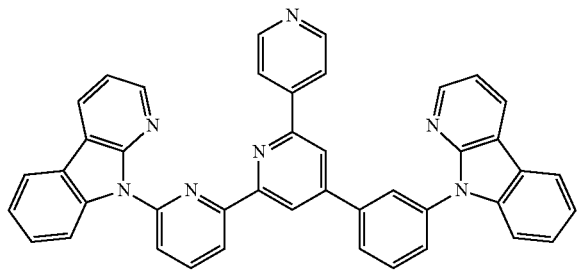
[Chem. 94]
(Compound 94)
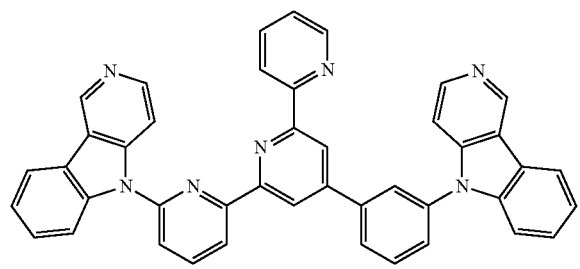
[Chem. 95]
(Compound 95)
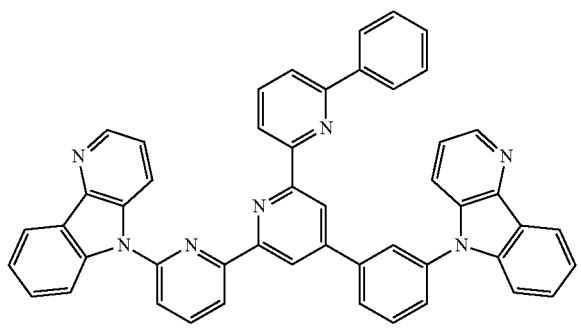
[Chem. 96]
(Compound 96)
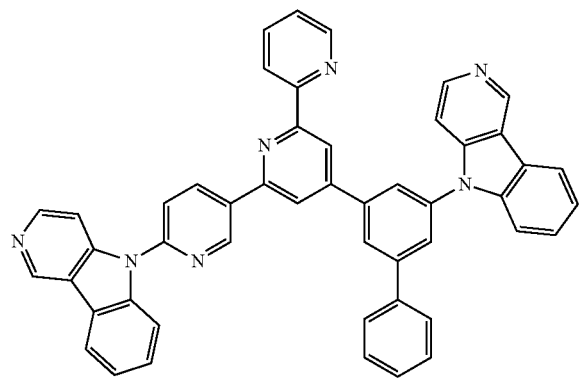
[Chem. 97]
(Compound 97)
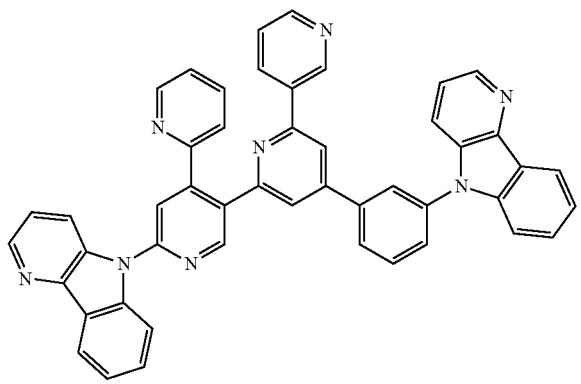

-continued
(Compound 98)
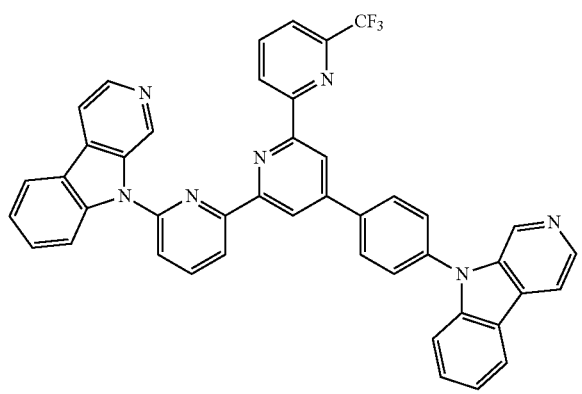
(Compound 99)
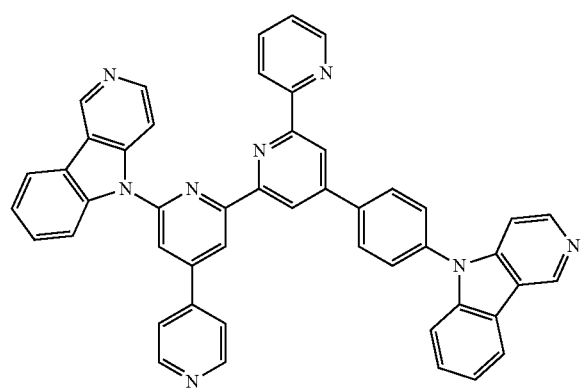
(Compound 100)
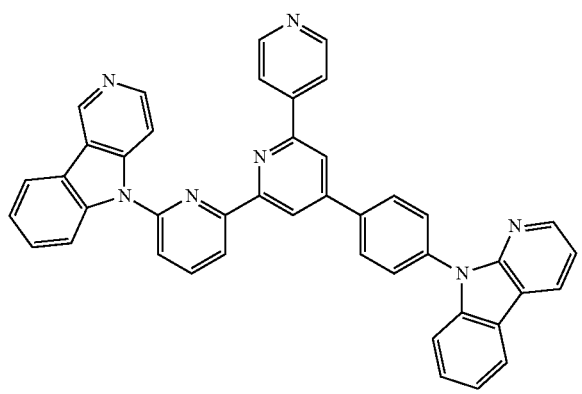
(Compound 101)
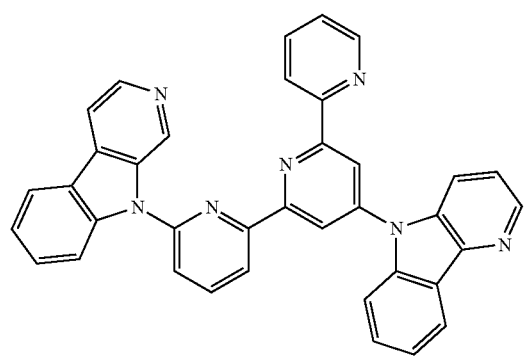
(Compound 102)
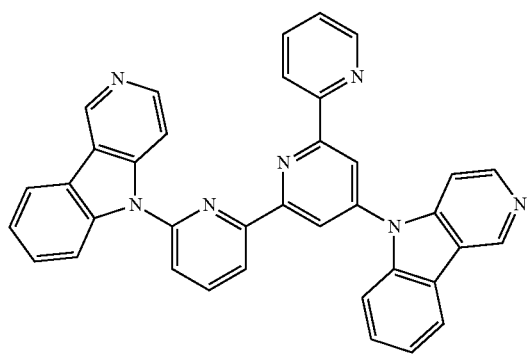
(Compound 103)
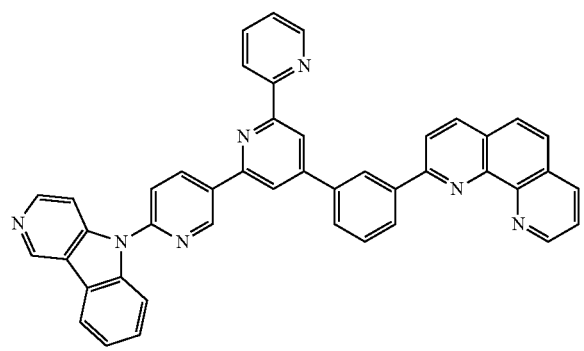

-continued
[Chem. 104]
(Compound 104)
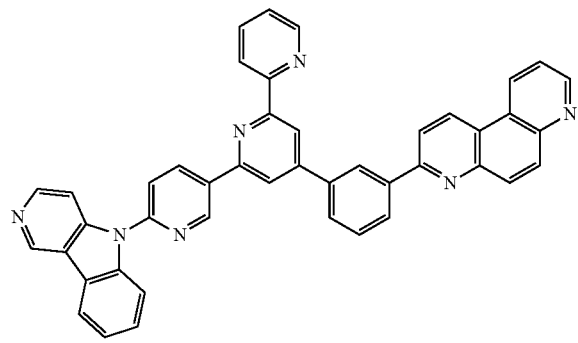
[Chem. 105]
(Compound 105)
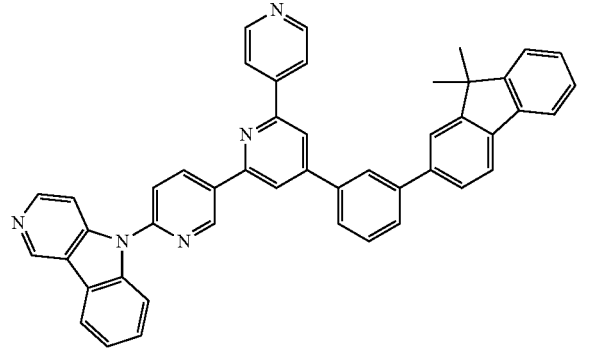
[Chem. 106]
(Compound 106)
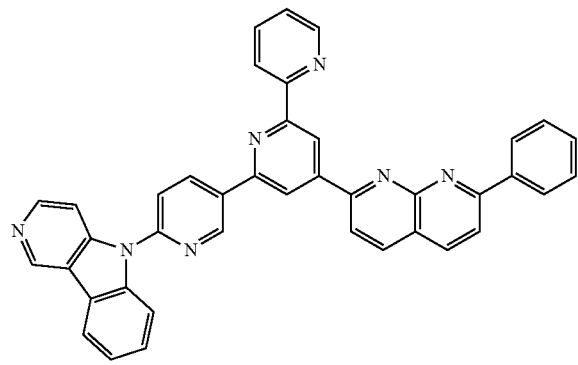
[Chem. 107]
(Compound 107)
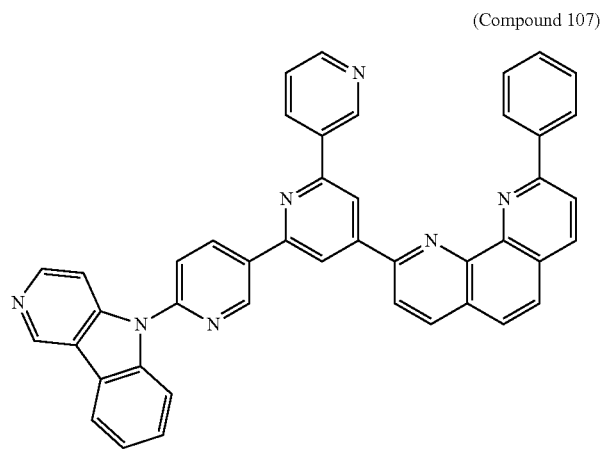
[Chem. 108]
(Compound 108)
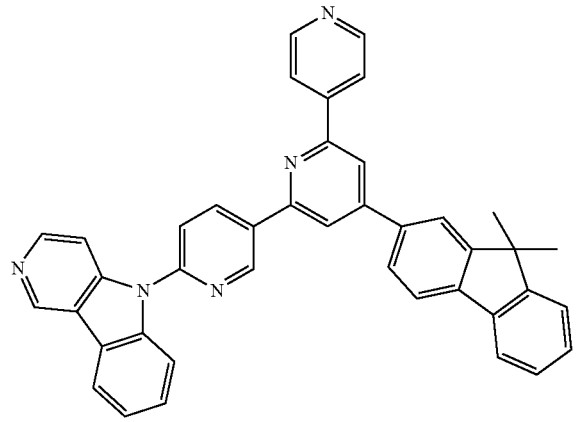
[Chem. 109]
(Compound 109)
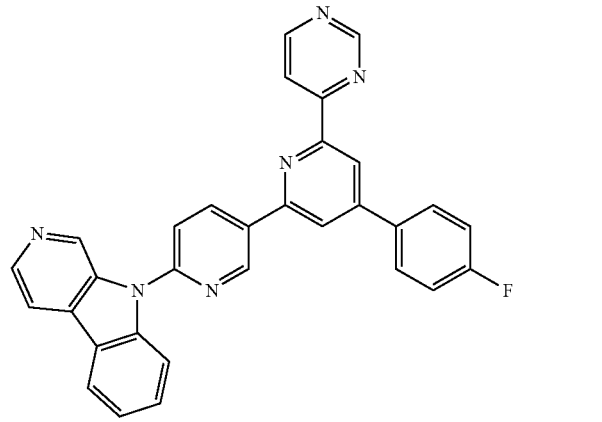

-continued
[Chem. 110]
(Compound 110)
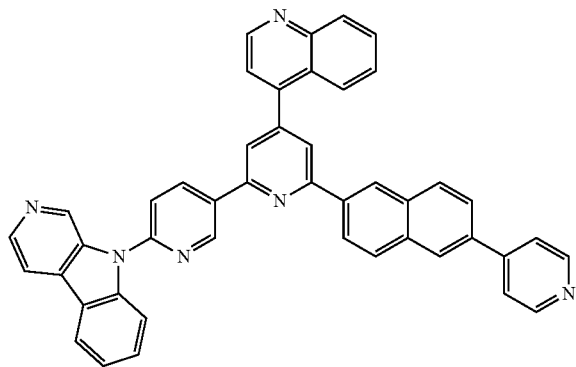
[Chem. 111]
(Compound 111)
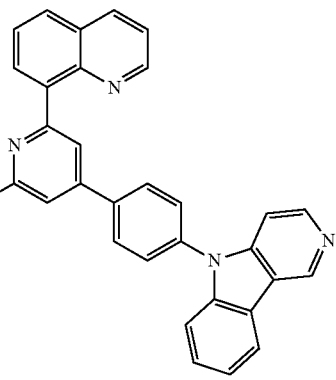
[Chem. 112]
(Compound 112)
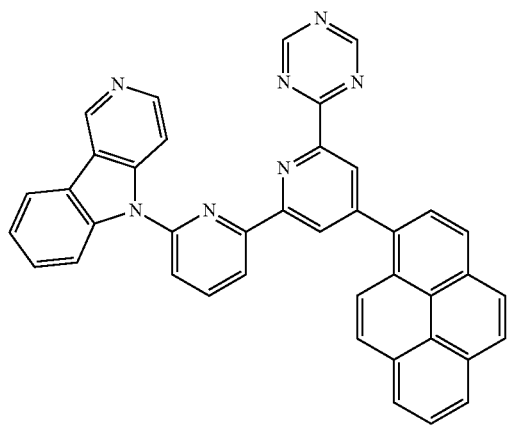
[Chem. 113]
(Compound 113)
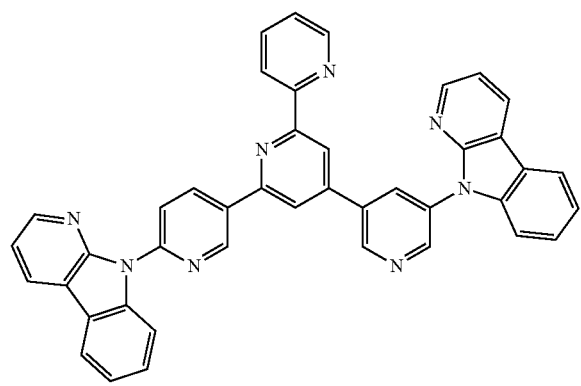
[Chem. 114]
(Compound 114)
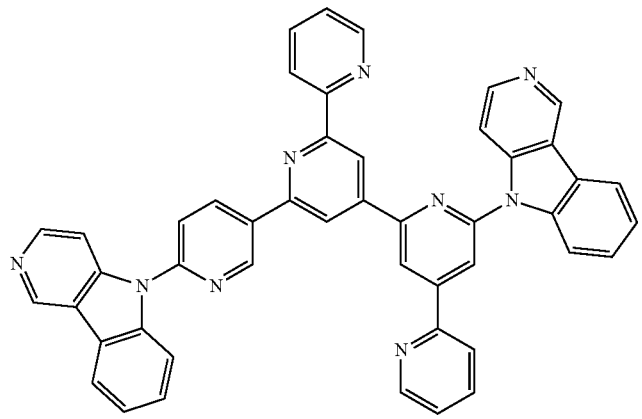

-continued
[Chem. 115]
(Compound 115)
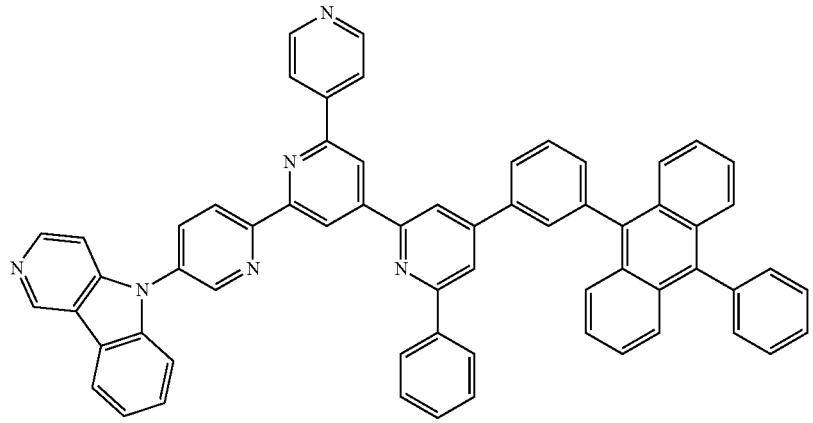
[Chem. 116]
(Compound 116)
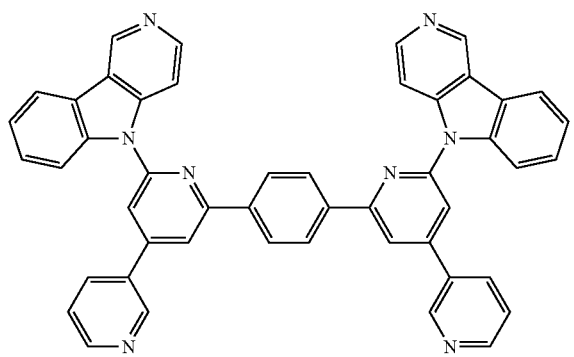
[Chem. 117]
(Compound 117)
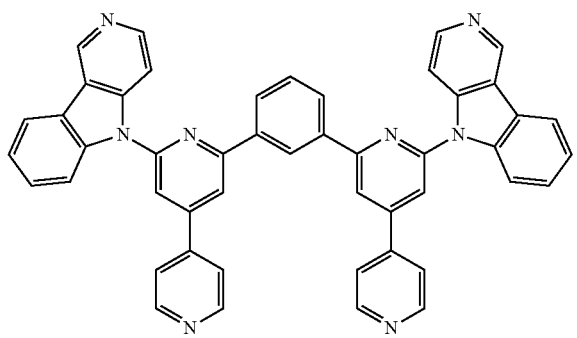
[Chem. 118]
(Compound 118)
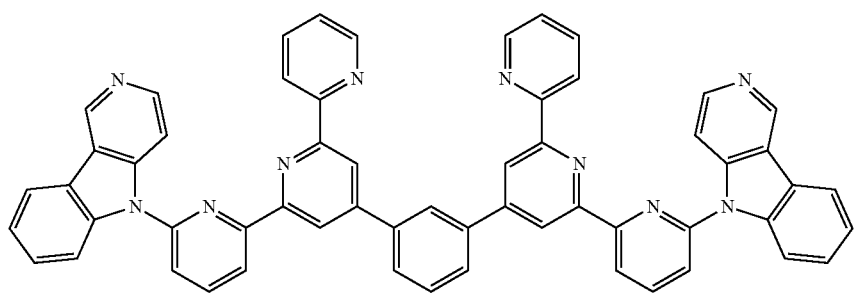
[Chem. 119]
(Compound 119)
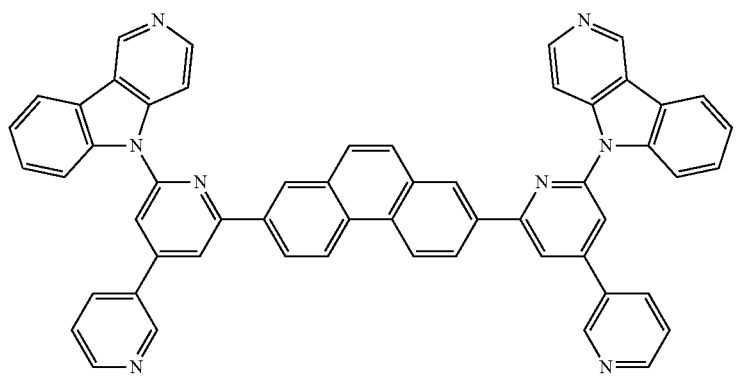

-continued
[Chem. 120]
(Compound 120)
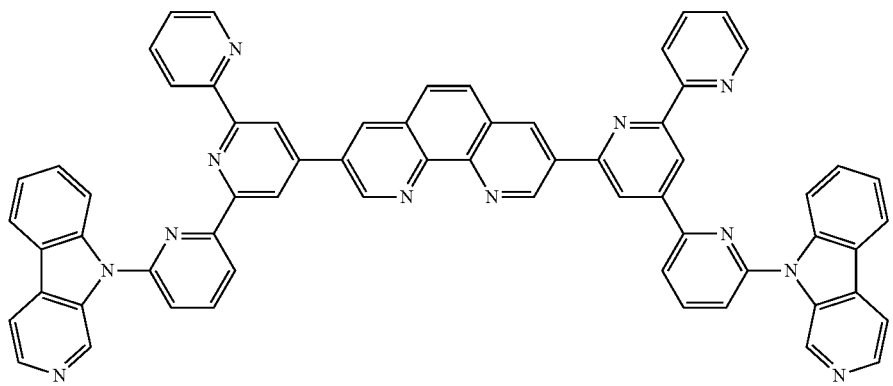
[Chem. 121]
(Compound 121)
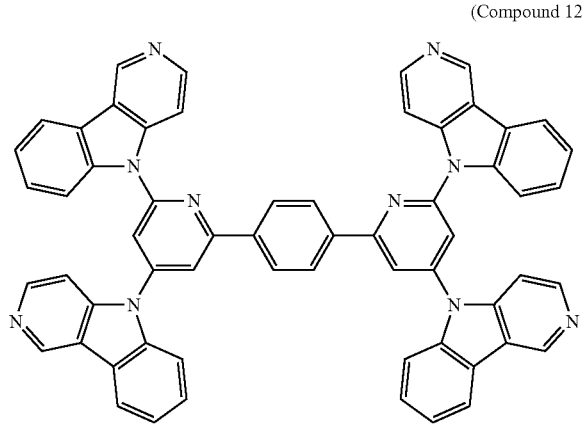
[Chem. 122]
(Compound 122)
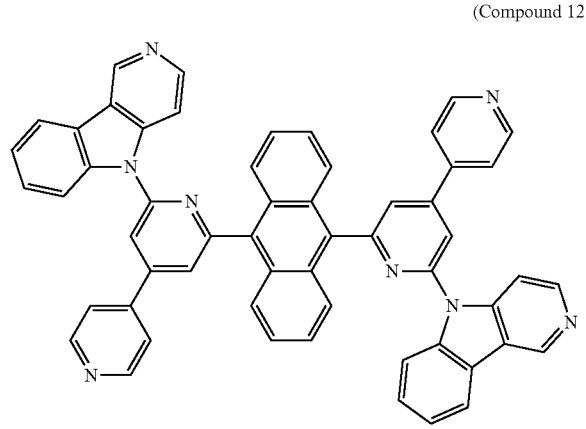
[Chem. 123]
(Compound 123)
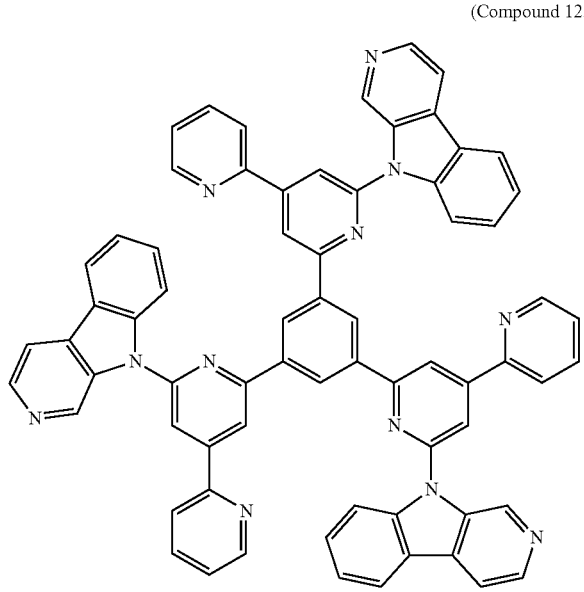
[Chem. 124]
(Compound 124)
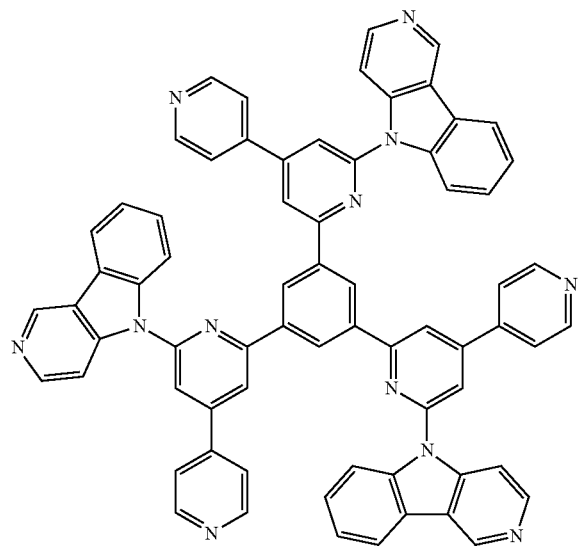

-continued
[Chem. 125]
(Compound 125)
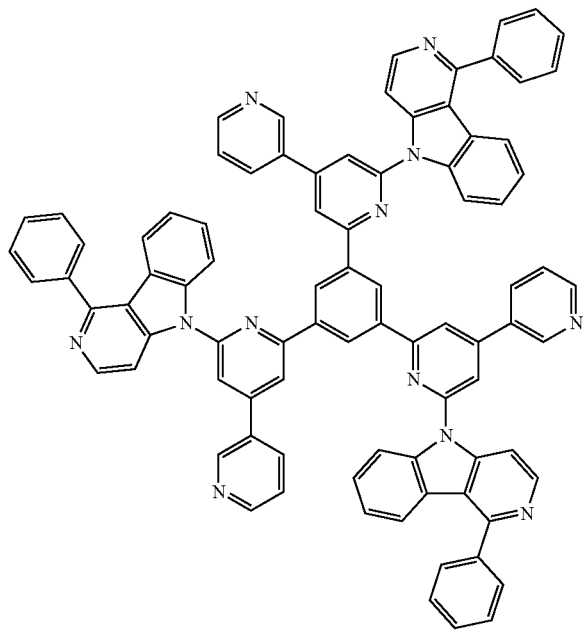
[Chem. 126]
(Compound 126)
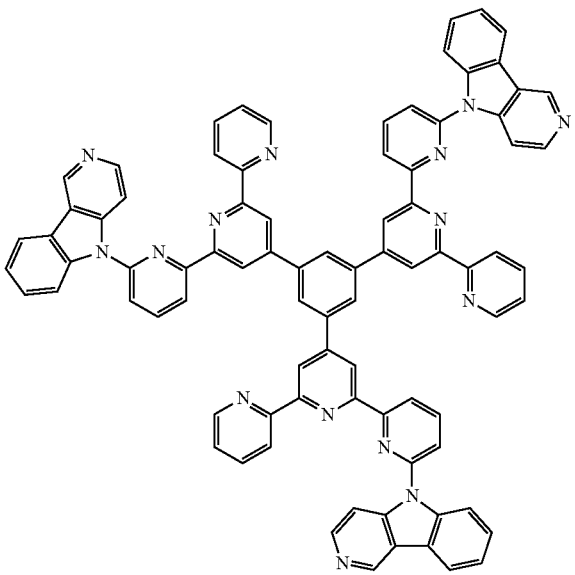
[Chem. 127]
(Compound 127)
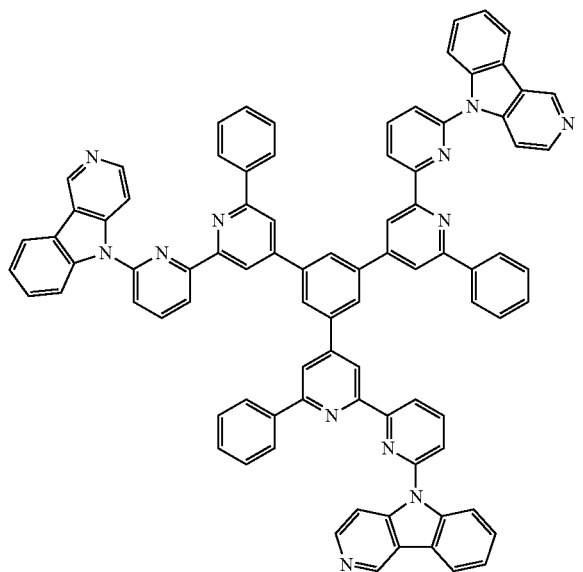
[Chem. 128]
(Compound 128)
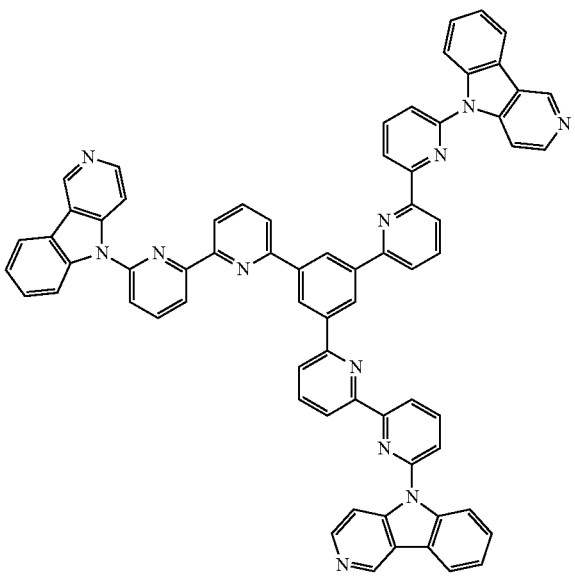

[Chem. 129]
(Compound 129)
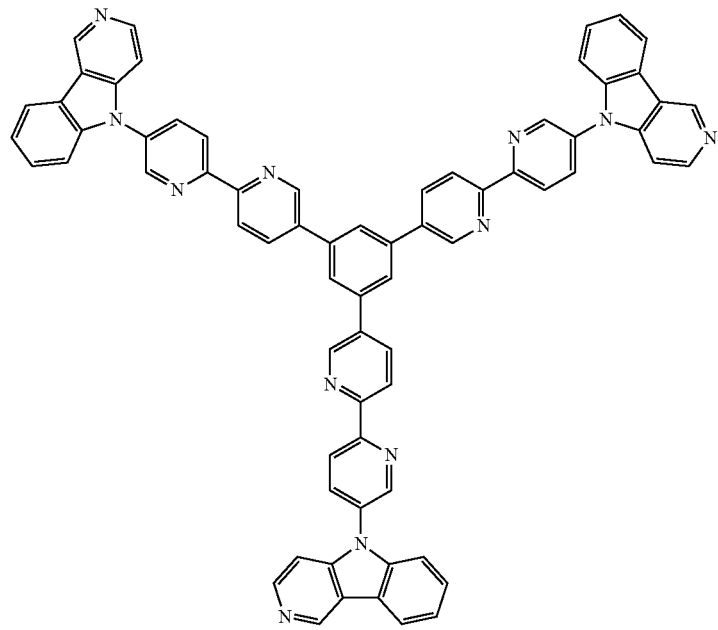
[Chem. 130]
(Compound 130)
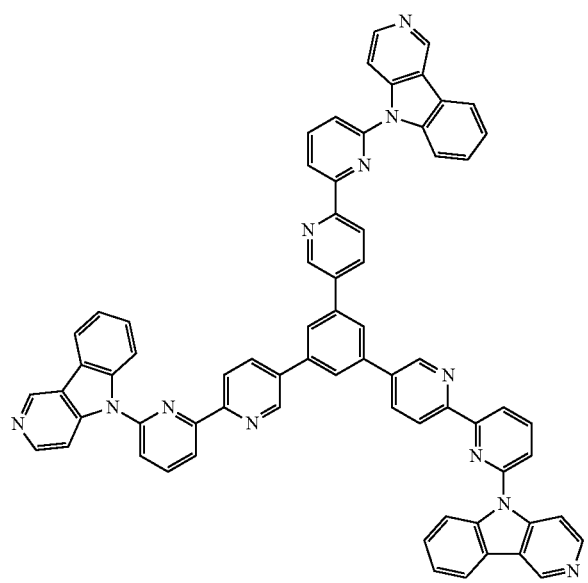
[Chem. 131]
(Compound 131)
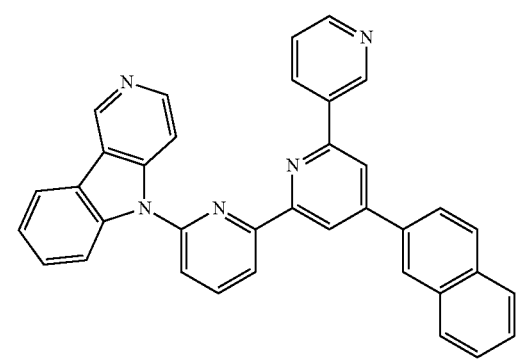

[Chem. 132]

(Compound 132)

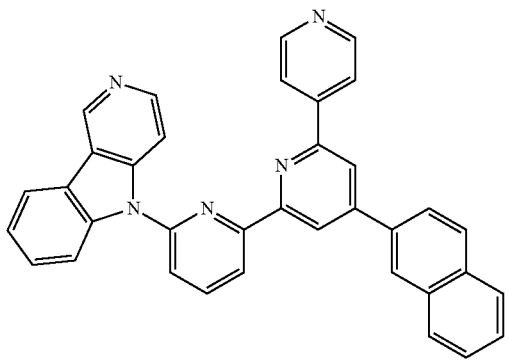

[Chem. 133]

(Compound 133)

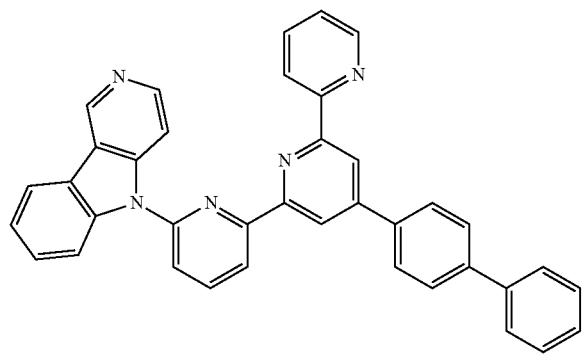

[Chem. 134]

(Compound 134)

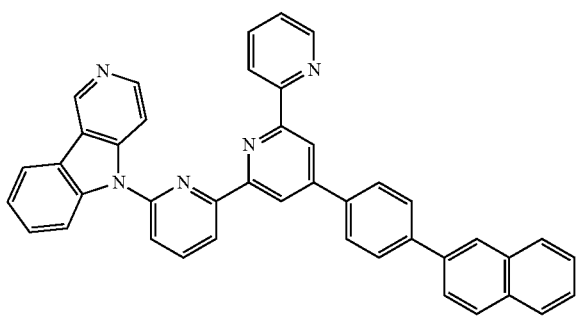

[Chem. 135]

(Compound 135)

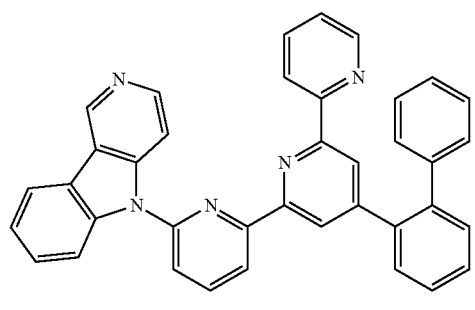

[Chem. 136]

(Compound 136)

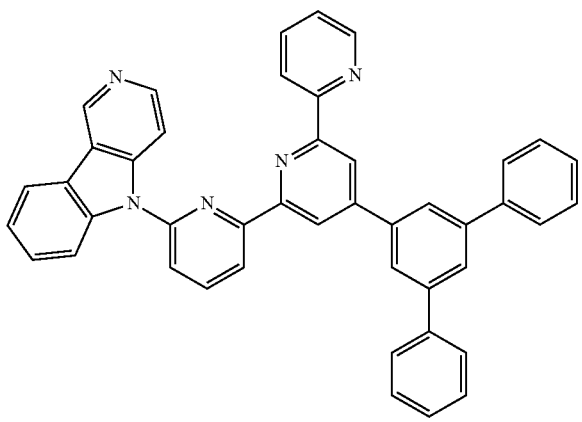

Purification of these compounds was performed by purification by column chromatography, adsorption purification with active carbon, activated clay, or the like, a recrystallization or crystallization method with a solvent, or the like. Identification of the compounds was performed by NMR analysis. As physical properties, DSC measurement (Tg) and melting point measurement were carried out. The melting point serves as an indicator of vapor deposition properties, and the glass transition point (Tg) serves as an indicator of stability in a thin-film state.

The melting point and the glass transition point were measured using a powder material by means of a highly sensitive differential scanning calorimeter DSC 3100S manufactured by Bruker AXS.

Further, the work function was measured by preparing a thin film of 100 nm on an ITO substrate and using a photoelectron spectroscopy in air (Model AC-3, manufactured by Riken Keiki Co., Ltd.). The work function is regarded as an indicator of hole-blocking ability.

Examples of the structure of the organic EL device of the invention include a structure having an anode, a hole-injecting layer, a hole-transporting layer, an emitting layer, a hole-blocking layer, an electron-transporting layer and a cathode in this order on a substrate, and a structure further having an electron-injecting layer between the electron-transporting layer and the cathode. In these multilayer structures, it is possible to omit several layers of the organic layers and, for example, the structure may have a constitution sequentially having an anode, a hole-transporting layer, an emitting layer, an electron-transporting layer and a cathode on a substrate.

As the anode of the organic EL device, an electrode material having a large work function, such as ITO or gold, is used. As the hole-injecting layer, besides copper phthalocyanine (hereinafter referred to as CuPc), materials such as star-burst type triphenylamine derivatives and wet-process type materials may be employed.

For the hole-transporting layer, there may be used N,N'-diphenyl-N,N'-di(m-tolyl)-benzidine (hereinafter referred to as TPD) and N,N'-diphenyl-N,N'-di(α-naphthyl)-benzidine (hereinafter referred to as NPD), which are one of benzidine derivatives, various triphenylamine tetramers, and the like. Further, as the hole-injecting/transporting layers, wet-process type polymer materials such as PEDOT/PSS may be employed.

As the emitting layer, hole-blocking layer, and electron-transporting layer of the organic EL device of the invention, besides the compound having a pyridoindole ring structure bonded with a substituted pyridyl group, aluminum complexes, thiazole derivatives, oxazole derivatives, carbazole derivatives, polydialkylfluorene derivatives, and the like may be used.

By using a conventional luminescence material such as an aluminum complex or styryl derivative for the emitting layer and using the compound having a pyridoindole ring structure bonded with a substituted pyridyl group as the hole-blocking layer and the electron-transporting layer, a high-performance organic EL device can be prepared. Further, a high-performance organic EL device can be prepared also by adding a dopant, for example, a fluorescent material such as quinacridone, coumarin or rubrene or a phosphorescent material such as an iridium complex of phenylpyridine, as a host material of the emitting layer.

Furthermore, the compound having a pyridoindole ring structure bonded with a substituted pyridyl group can be used as the electron-transporting layer through multilayering or co-deposition with conventional electron-transporting material(s).

The organic EL device of the invention may have an electron-injecting layer. As the electron-injecting layer, lithium fluoride or the like may be used. For the cathode, an electrode material having a low work function such as aluminum, or an alloy having a low work function such as aluminum magnesium is used as an electrode material.

Embodiments of the invention will be illustrated in greater detail with reference to the following Examples, but the invention should not be construed as being limited thereto so long as not exceeding the gist of the invention.

Example 1

Synthesis of 4'-(naphthalen-2-yl)-6-(5H-pyrido[4,3-b]indol-5-yl)-[2,2';6',2"]terpyridine (Compound 27)

A reaction vessel was charged with 11.0 g of 2-acetyl-6-bromopyridine, 14.0 g of iodine, and 45 mL of pyridine, followed by heating and stirring at 100° C. for 5 hours. After cooling to room temperature, 100 mL of water was added thereto and purification by recrystallization was performed. The reaction product was vacuum-dried at 70° C. for 12 hours to obtain 13.8 g (yield, 62%) of [2-(6-bromopyridin-2-yl)oxoethyl]pyridinium iodide as a brown powder.

Subsequently, 25.8 g of 2-naphthaldehyde, 20.0 g of 2-acetylpyridine, and 250 mL to methanol were mixed together, and the mixture was cooled to −5° C. with stirring. Thereto was added dropwise 250 mL of 3 wt % NaOH/methanol solution, followed by stirring at −5° C. for 3 hours and then further carrying out a reaction at the same temperature for 1 day. The crude product was collected by filtration and then washed with methanol to obtain 37.1 g (yield, 86%) of 3-(naphthalen-2-yl)-1-(pyridin-2-yl)propenone as a yellow powder.

To 13.5 g of the [2-(6-bromopyridin-2-yl)oxoethyl]pyridinium iodide were added 32.1 g of ammonium acetate and 180 mL of methanol, followed by dissolving with stirring at 50° C. Thereafter, 8.7 g of the 3-(naphthalen-2-yl)-1-(pyridin-2-yl)propenone was added thereto, followed by stirring for further 1 day. After cooling to room temperature, the crude product was collected by filtration and then washed with methanol. This product was vacuum-dried at 70° C. for 12 hours to obtain 4.2 g (yield, 28%) of 6-bromo-4'-(naphthalen-2-yl)-[2,2';6',2"]terpyridine as a yellow-brown powder.

To 4.2 g of the resulting 6-bromo-4'-(naphthalen-2-yl)-[2,2';6',2"]terpyridine were added 1.6 g of 5H-pyrido[4,3-b]indole, 0.3 g of a copper powder, 4.0 g of potassium carbonate, 0.3 mL of dimethyl sulfoxide, and 10 mL of n-dodecane, followed by heating and stirring at 150° C. for 8 hours. After cooling to room temperature, 80 mL of chloroform was added thereto to remove an insoluble matter by filtration, and the filtrate was concentrated under a reduced pressure to obtain a crude product. The crude product was purified by column chromatography (carrier: NH silica gel, eluent: hexane/chloroform) to obtain 2.2 g (yield, 43%) of 4'-(naphthalen-2-yl)-6-(5H-pyrido[4,3-b]indol-5-yl)-[2,2';6',2"]terpyridine (Compound 27) as a white powder.

The structure of the white powder obtained was identified using NMR. The results of the $^1$H-NMR measurement are shown in FIG. 1.

The following 23 hydrogen signals were detected by $^1$H-NMR (CDCl$_3$-CD$_3$OD). δ(ppm)=9.35 (1H), 8.88 (2H), 8.72-8.79 (3H), 8.52 (1H), 8.36 (1H), 8.25 (1H), 8.21 (1H), 7.87-8.01 (7H), 7.72 (1H), 7.52-7.59 (3H), 7.43-7.47 (2H).

Example 2

Synthesis of 4'-(naphthalen-2-yl)-6-(5H-pyrido[4,3-b]indol-5-yl)-[2,2';6',3"]terpyridine (Compound 131)

As in Example 1,3-(naphthalen-2-yl)-1-(pyridin-3-yl)propenone was synthesized from 2-naphthaldehyde and 3-acetylpyridine, and further subjected to a reaction with [2-(6-bromopyridin-2-yl)oxoethyl]pyridinium iodide to synthesize 6-bromo-4'-(naphthalen-2-yl)-[2,2';6',3"]terpyridine. To 4.4 g of the resulting 6-bromo-4'-(naphthalen-2-yl)-[2,2'; 6',3"]terpyridine were added 1.7 g of 5H-pyrido[4,3-b]indole, 0.3 g of a copper powder, 4.2 g of potassium carbonate, 0.3 mL of dimethyl sulfoxide, and 20 mL of o-dichlorobenzene, followed by heating and stirring at 140° C. for 3 hours. After cooling to room temperature, 50 mL of chloroform was added thereto to remove an insoluble matter by filtration, and the filtrate was concentrated under a reduced pressure to obtain a crude product. The crude product was dissolved in chloroform and subjected to adsorptive purification with NH silica gel and then to recrystallization using o-dichlorobenzene. Thus, 2.9 g (yield, 55%) of 4'-(naphthalen-2-yl)-6-(5H- pyrido[4,3-b]indol-5-yl)-[2,2';6',3"]terpyridine (Compound 131) was obtained as a white powder.

Figure 2:
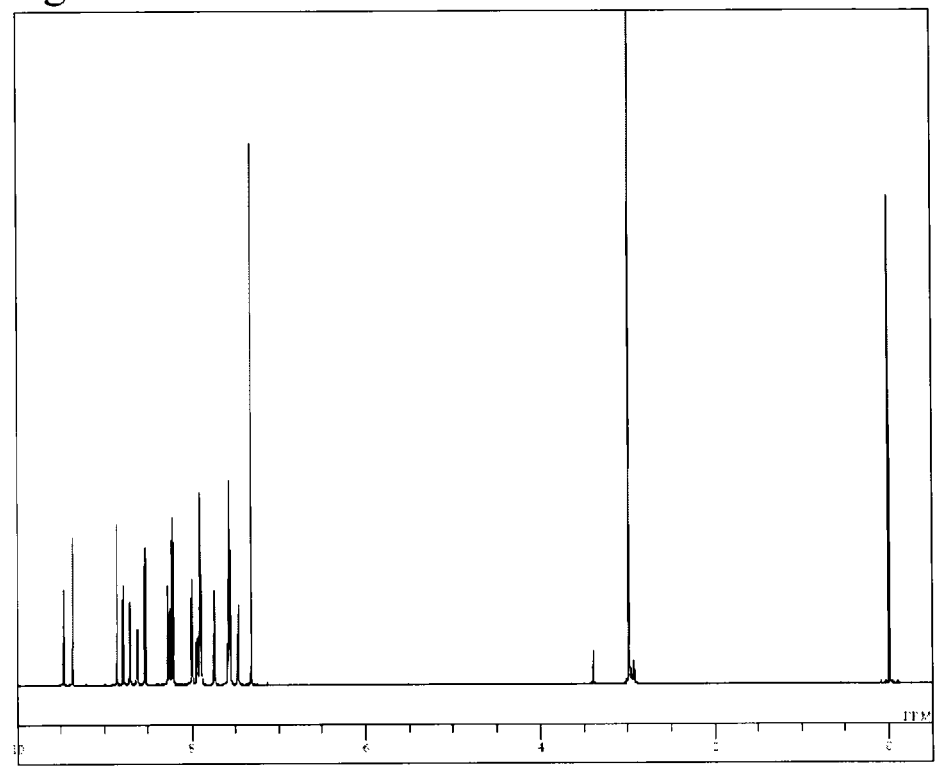
FIG. 2 is a $^1$H-NMR chart of the compound (Compound 131) of Invention Example 2.

The structure of the white powder obtained was identified using NMR. The results of $^1$H-NMR measurement are shown in FIG. 2.

The following 23 hydrogen signals were detected by $^1$H-NMR (CDCl$_3$-CD$_3$OD). δ(ppm)=9.47 (1H), 9.37 (1H), 8.86 (1H), 8.78 (1H), 8.68-8.72 (1H), 8.60-8.64 (1H), 8.54 (1H), 8.18-8.29 (4H), 7.86-8.01 (6H), 7.74 (1H), 7.52-7.59 (4H), 7.47 (1H).

Example 3

Synthesis of 4'-(naphthalen-2-yl)-6-(5H-pyrido[4,3-b]indol-5-yl)-[2,2';6',4"]terpyridine (Compound 132)

As in Example 1,3-(naphthalen-2-yl)-1-(pyridin-4-yl)propenone was synthesized from 2-naphthaldehyde and 4-acetylpyridine, and further subjected to a reaction with [2-(6-bromopyridin-2-yl)oxoethyl]pyridinium iodide to synthesize 6-bromo-4'-(naphthalen-2-yl)-[2,2';6',4"]terpyridine. To 5.0 g of the resulting 6 bromo-4'-(naphthalen-2-yl)-[2,2'; 6',4"]terpyridine were added 1.9 g of 5H-pyrido[4,3-b]indole, 0.4 g of a copper powder, 4.7 g of potassium carbonate, 0.4 mL of dimethyl sulfoxide, and 22 mL of o-dichlorobenzene, followed by heating and stirring at 140° C. for 5.5 hours. After cooling to room temperature, 800 mL of chloroform was added thereto to remove an insoluble matter by filtration, and the filtrate was concentrated under a reduced pressure to obtain a crude product. The crude product was dissolved in chloroform and subjected to adsorptive purification with NH silica gel and then to recrystallization using o-dichlorobenzene. Thus, 5.1 g (yield, 85%) of 4'-(naphthalen-2-yl)-6-(5H-pyrido[4,3-b]indol-5-yl)-[2,2';6',4"]terpyridine (Compound 132) was obtained as a white powder.

Figure 3:
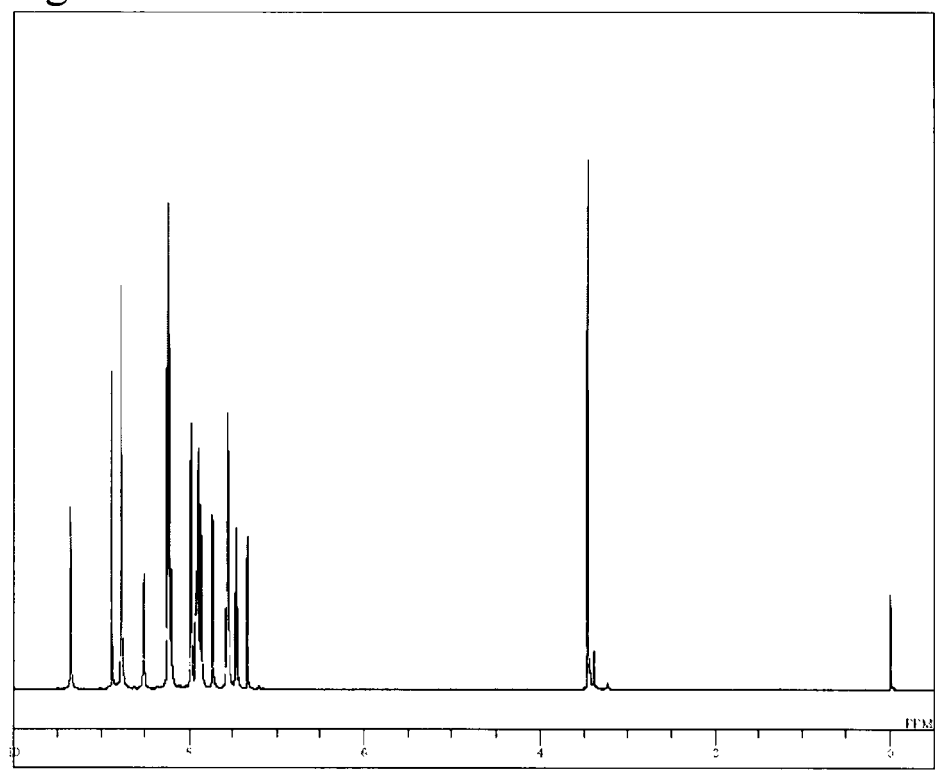
FIG. 3 is a $^1$H-NMR chart of the compound (Compound 132) of Invention Example 3.

The structure of the white powder obtained was identified using NMR. The results of $^1$H-NMR measurement are shown in FIG. 3.

The following 23 hydrogen signals were detected by $^1$H-NMR (CDCl$_3$-CD$_3$OD). δ(ppm)=9.35 (1H), 8.88 (1H), 8.73-8.80 (3H), 8.52 (1H), 8.17-8.27 (6H), 7.83-8.00 (6H), 7.74 (1H), 7.52-7.58 (3H), 7.46 (1H).

Example 4

Synthesis of 4'-(biphenyl-4-yl)-6-(5H-pyrido[4,3-b]indol-5-yl)-[2,2';6',2"]terpyridine (Compound 133)

As in Example 1,3-(4-bromophenyl)-1-(pyridin-2-yl)propenone was synthesized from 4-bromobenzaldehyde and 2-acetylpyridine, and further subjected to a reaction with [2-(6-bromopyridin-2-yl)oxoethyl]pyridinium iodide to synthesize 6-bromo-4'-(4-bromophenyl)-[2,2';6',2"]terpyridine. To 15.3 g of the resulting 6-bromo-4'-(4-bromophenyl)-[2,2'; 6',2"]terpyridine were added 5.6 g of 5H-pyrido[4,3-b]indole, 1.0 g of a copper powder, 6.8 g of potassium carbonate, 1.0 mL of dimethyl sulfoxide, and 80 mL of o-dichlorobenzene, followed by heating and stirring at 120° C. for 7 hours. After cooling to room temperature, 200 mL of chloroform was added thereto to remove an insoluble matter by filtration, and the filtrate was concentrated under a reduced pressure to obtain a concentrate. To the concentrate, 2 L of toluene was added and insoluble matter was removed by filtration. NH silica gel was added to the filtrate to perform adsorptive purification. Thereafter, the filtrate was concentrated under a reduced pressure to obtain a crude product. The crude product obtained was washed with methanol to obtain 11.3 g (yield, 62%) of 4'-(4-bromophenyl)-6-(5H-pyrido[4,3-b]indol-5-yl)-[2,2';6',2"]terpyridine as a brown powder.

To 5.1 g of the resulting 4'-(4-bromophenyl)-6-(5H-pyrido[4,3-b]indol-5-yl)-[2,2';6',2"]terpyridine were added 1.1 g of phenylboronic acid, 0.5 g of tetrakis(triphenylphosphine)palladium, 23 mL of a 2 M aqueous potassium carbonate solution, 72 mL of toluene, and 18 mL of ethanol, followed by heating with reflux while stirring for 5.5 hours. After cooling to room temperature, a precipitate was collected by filtration. To the precipitate, 200 mL of chloroform was added and insoluble matter was removed by filtration. The filtrate was concentrated under a reduced pressure to obtain a concentrate. The concentrate was dissolved in chloroform and subjected to adsorptive purification with NH silica gel. Thereafter, the filtrate was concentrated under a reduced pressure to obtain a crude product. The crude product was washed with methanol to obtain 2.9 g (yield, 57%) of 4'-(biphenyl-4-yl)-6-(5H-pyrido[4,3-b]indol-5-yl)-[2,2';6',2"]terpyridine (Compound 133) as a white powder.

Figure 4:
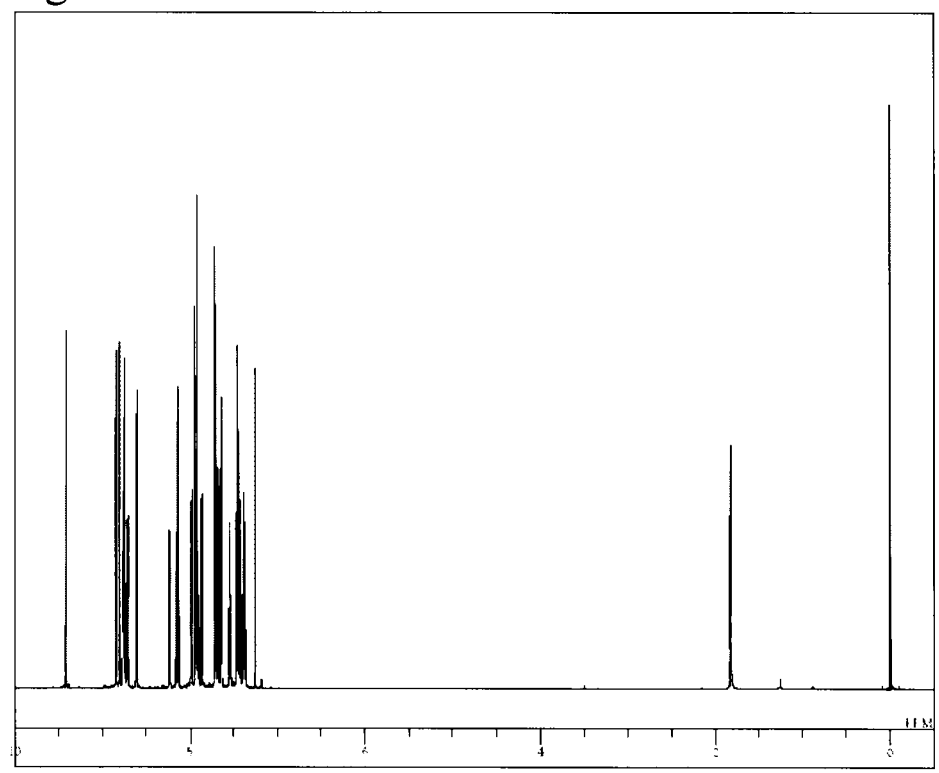
FIG. 4 is a $^1$H-NMR chart of the compound (Compound 133) of Invention Example 4.

The structure of the white powder obtained was identified using NMR. The results of $^1$H-NMR measurement are shown in FIG. 4.

The following 25 hydrogen signals were detected by $^1$H-NMR (CDCl$_3$). δ(ppm)=9.42 (1H), 8.85 (1H), 8.81 (1H), 8.69-8.78 (3H), 8.61 (1H), 8.23 (1H), 8.15 (1H), 7.99 (1H), 7.89-7.95 (3H), 7.86 (1H), 7.61-7.73 (5H), 7.54 (1H), 7.35-7.47 (5H).

Example 5

Synthesis of 4'-(4-naphthalen-2-yl-phenyl)-6-(5H-pyrido[4,3-b]indol-5-yl)-[2,2';6',2"]terpyridine (Compound 134)

To 4.6 g of the 4'-(4-bromophenyl)-6-(5H-pyrido[4,3-b]indol-5-yl)-[2,2';6',2"]terpyridine obtained in Example 4 were added 1.4 g of 2-naphthaleneboronic acid, 0.5 g of tetrakis(triphenylphosphine)palladium, 21 mL of a 2 M aqueous potassium carbonate solution, 72 mL of toluene, and 18 mL of ethanol, followed by heating with reflux while stirring for 6 hours. After cooling to room temperature, a precipitate was collected by filtration. To the precipitate, 200 mL of o-dichlorobenzene was added and insoluble matter was removed by filtration. The filtrate was concentrated under a reduced pressure to obtain a concentrate. The concentrate was dissolved in chloroform and subjected to adsorptive purification with NH silica gel. Thereafter, the filtrate was concentrated under a reduced pressure to obtain a crude product. The crude product was washed with ethyl acetate to obtain 3.5 g (yield, 69%) of 4'-(4-naphthalen-2-yl-phenyl)-6-(5H-pyrido[4,3-b]indol-5-yl)-[2,2';6',2"]terpyridine (Compound 134) as a white powder.

Figure 5:
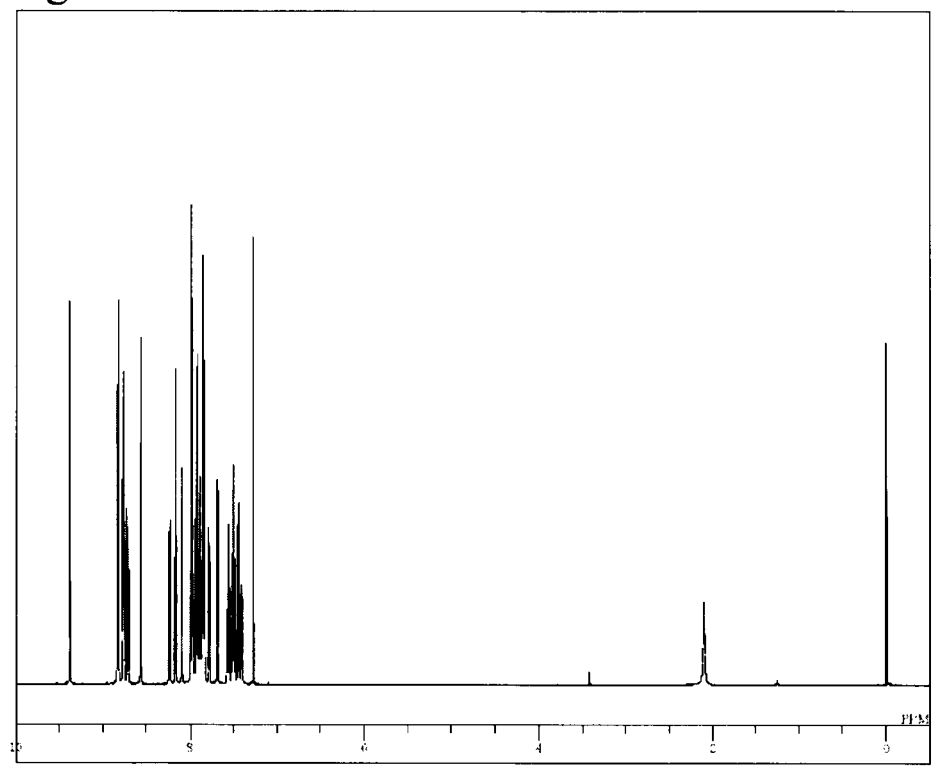
FIG. 5 is a $^1$H-NMR chart of the compound (Compound 134) of Invention Example 5.

The structure of the white powder obtained was identified using NMR. The results of $^1$H-NMR measurement are shown in FIG. 5.

The following 27 hydrogen signals were detected by $^1$H-NMR (CDCl$_3$-CD$_3$OD). δ(ppm)=9.38 (1H), 8.70-8.85 (5H), 8.57 (1H), 8.24 (1H), 8.17 (1H), 8.10 (1H), 7.84-8.01 (10H), 7.77-7.80 (1H), 7.69 (1H), 7.37-7.57 (5H).

Example 6

Synthesis of 4'-(biphenyl-2-yl)-6-(5H-pyrido[4,3-b]indol-5-yl)-[2,2';6',2"]terpyridine (Compound 135)

As in Example 1,3-(biphenyl-2-yl)-1-(pyridin-2-yl)propenone was synthesized from 2-biphenylcarboxyaldehyde and 2-acetylpyridine, and further subjected to a reaction with [2-(6-bromopyridin-2-yl)oxoethyl]pyridinium iodide to synthesize 4'-(biphenyl-2-yl)-6-bromo[2,2';6',2"]terpyridine. To 4.6 g of the resulting 4'-(biphenyl-2-yl)-6-bromo[2,2';6',2"]terpyridine were added 1.7 g of 5H-pyrido[4,3-b]indole, 0.3 g of a copper powder, 4.2 g of potassium carbonate, 0.3 mL of dimethyl sulfoxide, and 20 mL of o-dichlorobenzene, followed by heating and stirring at 140° C. for 5 hours. After cooling to room temperature, 60 mL of chloroform was added thereto to remove an insoluble matter by filtration, and the filtrate was concentrated under a reduced pressure to obtain a concentrate. The concentrate was dissolved in chloroform, and subjected to adsorptive purification with NH silica gel and to concentration under a reduced pressure to obtain a crude product. The crude product was washed with methanol and further washed with ethyl acetate to obtain 2.6 g (yield, 46%) of 4'-(biphenyl-2-yl)-6-(5H-pyrido[4,3-b]indol-5-yl)-[2,2';6',2"]terpyridine (Compound 135) as a white powder.

Figure 6:
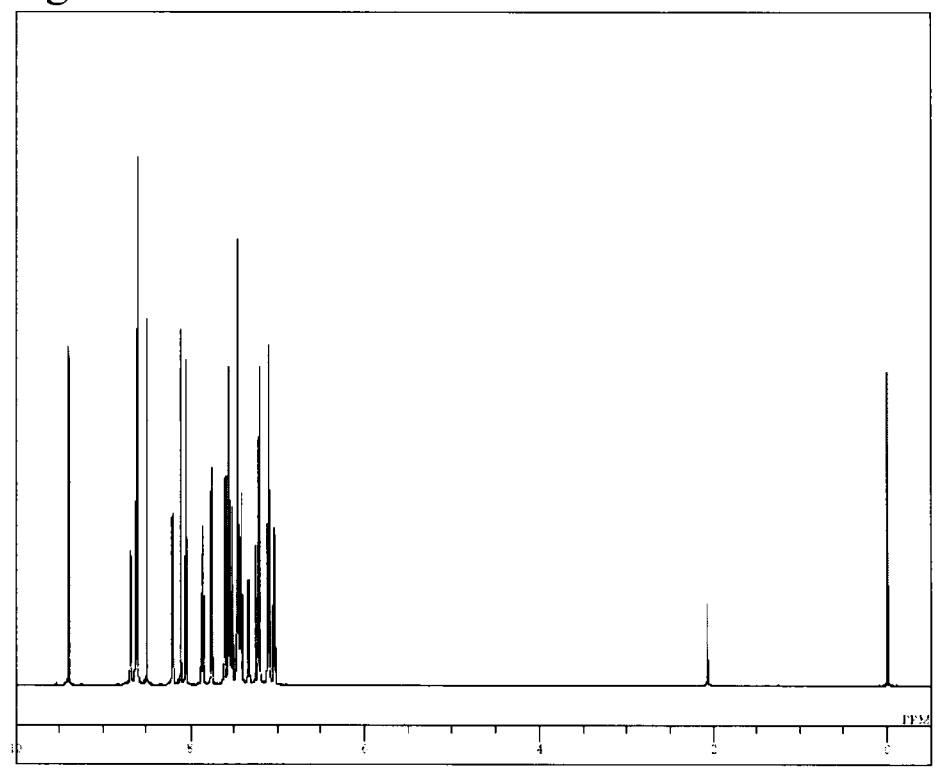
FIG. 6 is a $^1$H-NMR chart of the compound (Compound 135) of Invention Example 6.

The structure of the white powder obtained was identified using NMR. The results of $^1$H-NMR measurement are shown in FIG. 6.

The following 25 hydrogen signals were detected by $^1$H-NMR (CDCl$_3$). δ(ppm)=9.39 (1H), 8.57-8.70 (4H), 8.50 (1H), 8.20 (1H), 8.11 (1H), 8.05 (1H), 7.83-7.90 (1H), 7.76 (1H), 7.38-7.63 (8H), 7.33 (1H), 7.21 (2H), 7.10 (2H), 7.03 (1H).

Example 7

Synthesis of 6-(5H-pyrido[4,3-b]indol-5-yl)-4'-[1,1';3',1"]terphenyl-5'-yl-[2,2';6',2"]terpyridine (Compound 136)

As in Example 4,3-(3,5-dibromophenyl)-1-(pyridin-2-yl)-propenone was synthesized from 3,5-dibromobenzaldehyde and 2-acetylpyridine, and further subjected to a reaction with [2-(6-bromopyridin-2-yl)oxoethyl]pyridinium iodide to synthesize 6-bromo-4'-(3,5-dibromophenyl)-[2,2';6',2"]terpyridine. This compound was further subjected to a reaction with 5H-pyrido[4,3-b]indole to synthesize 4'-(3,5-dibromophenyl)-6-(5H-pyrido[4,3-b]indol-5-yl)-[2,2';6',2"]terpyridine. To 5.1 g of the resulting 4'-(3,5-dibromophenyl)-6-(5H-pyrido[4,3-b]indol-5-yl)-[2,2';6',2"]terpyridine were added 2.1 g of phenylboronic acid, 0.5 g of tetrakis(triphenylphosphine) palladium, 20 mL of a 2 M aqueous potassium carbonate solution, 72 mL of toluene, and 18 mL of ethanol, followed by heating with reflux while stirring for 12 hours. After cooling to room temperature, the precipitate was collected by filtration. To the precipitate, 80 mL of chloroform was added and insoluble matter was removed by filtration. The filtrate was concentrated under a reduced pressure to obtain a crude product. The crude product was purified by column chromatography (carrier: NH silica gel, eluent: toluene) and then recrystallized using o-dichlorobenzene. Thus, 2.1 g (yield, 41%) of 6-(5H-pyrido[4,3-b]indol-5-yl)-4'-[1,1';3',1"]terphenyl-5'-yl-[2,2';6',2"]terpyridine (Compound 136) was obtained as a white powder.

Figure 7:
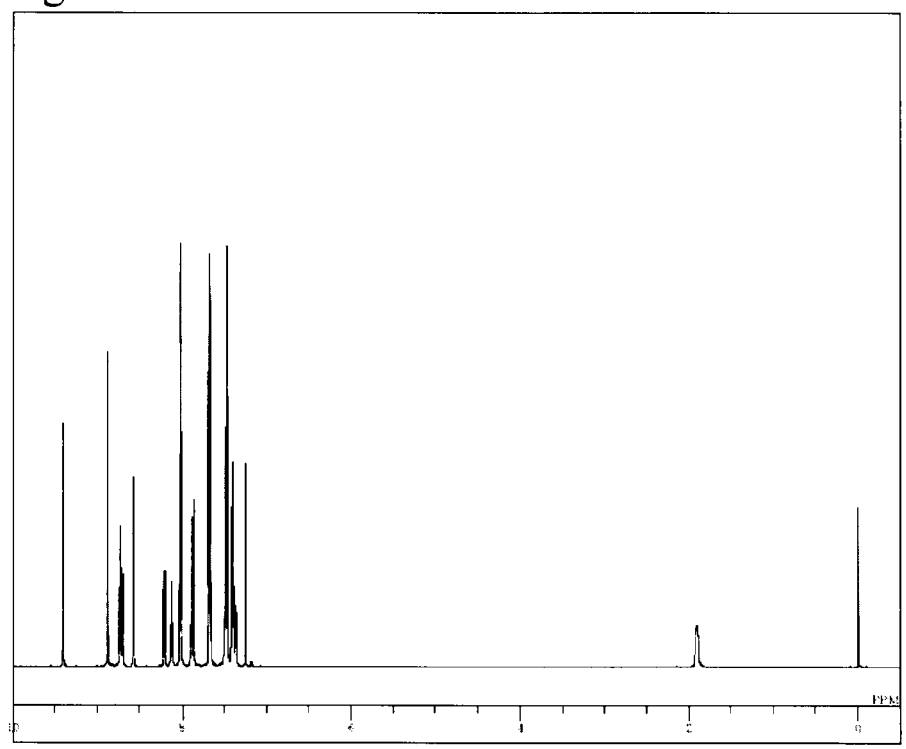
FIG. 7 is a $^1$H-NMR chart of the compound (Compound 136) of Invention Example 7.

The structure of the white powder obtained was identified using NMR. The results of $^1$H-NMR measurement are shown in FIG. 7.

The following 29 hydrogen signals were detected by $^1$H-NMR (CDCl$_3$). δ(ppm)=9.41 (1H), 8.88 (2H), 8.68-8.75 (3H), 8.57 (1H), 8.21 (1H), 8.13 (1H), 8.00-8.04 (3H), 7.85-7.91 (3H), 7.64-7.69 (5H), 7.45-7.51 (5H), 7.35-7.43 (4H).

Example 8

For the compounds of the invention, melting point and glass transition point were determined by means of a highly sensitive differential scanning calorimeter (DSC 3100S manufactured by Bruker AXS).

|  | Melting Point | Glass Transition Point |
| --- | --- | --- |
| Compound of Invention Example 1 | 281° C. | 103° C. |
| Compound of Invention Example 2 | 280° C. | Nil |
| Compound of Invention Example 3 | 301° C. | 110° C. |
| Compound of Invention Example 4 | 215° C. | 112° C. |
| Compound of Invention Example 5 | 154° C. | 122° C. |
| Compound of Invention Example 6 | 135° C. | 108° C. |
| Compound of Invention Example 7 | 247° C. | 124° C. |

The compounds of the invention had a glass transition point of 100° C. or higher or had no glass transition point. This indicates that a thin-film state is stable for the compounds of the invention.

Example 9

Using each of the compounds of the invention, a deposited film having a film thickness of 100 nm was prepared on an ITO substrate and work function was measured on a photoelectron spectroscopy in air (Model AC-3, manufactured by Riken Keiki Co., Ltd.).

|  | Work Function |
| --- | --- |
| Compound of Invention Example 1 | 6.27 eV |
| Compound of Invention Example 2 | 6.20 eV |
| Compound of Invention Example 3 | 6.22 eV |
| Compound of Invention Example 4 | 6.33 eV |
| Compound of Invention Example 5 | 6.26 eV |
| Compound of Invention Example 6 | 6.35 eV |
| Compound of Invention Example 7 | 6.31 eV |

Thus, the compounds of the invention have values deeper than a work function of 5.4 eV possessed by common hole-transporting materials such as NPD and TPD and have a large hole-blocking ability.

Example 10

Figure 8:
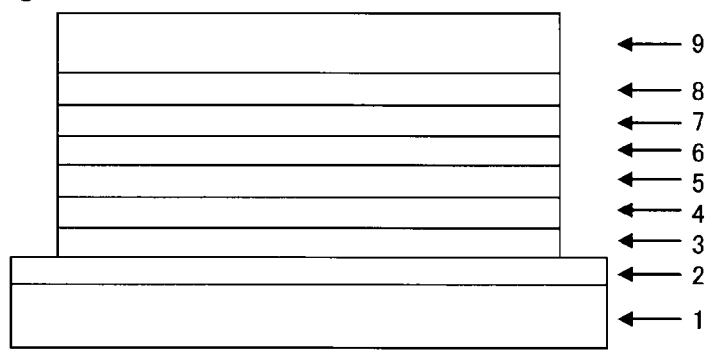
FIG. 8 is a drawing showing the constitution of the EL devices of Examples 10 to 17.
Figure 9:
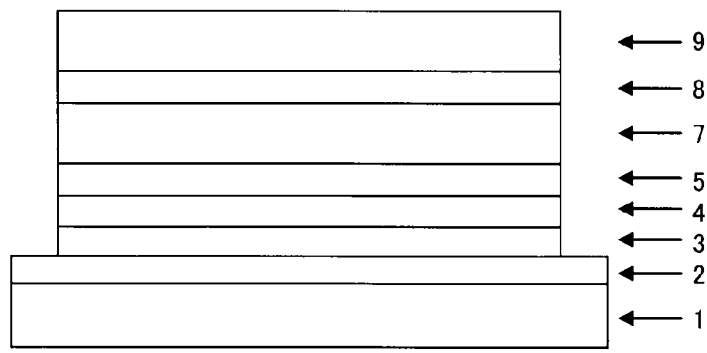
FIG. 9 is a drawing showing the constitution of the EL devices of Comparative Examples 1 and 2.

An organic EL device was produced so as to have a layer configuration including, as shown in FIG. 8, a glass substrate 1 having an ITO electrode formed thereon beforehand as a transparent anode 2, a hole-injecting layer 3, a hole-transporting layer 4, an emitting layer 5, a hole-blocking layer 6, an electron-transporting layer 7, an electron-injecting layer 8, and a cathode (aluminum electrode) 9 in this order.

Specifically, after the glass substrate 1 on which ITO having a film thickness of 150 nm had been formed was washed with an organic solvent, the surface thereof was then cleaned by a UV ozone treatment. It was mounted in a vacuum deposition machine, which was then evacuated to 0.001 Pa or lower. Subsequently, copper phthalocyanine was deposited thereon as the hole-injecting layer 3 at a deposition rate of 3.6 nm/min to a thickness of about 20 nm. NPD was deposited as the hole-transporting layer 4 on the hole-injecting layer 3 at a deposition rate of 3.6 nm/min to a thickness of about 40 nm. As the emitting layer 5, $Alq_3$ was deposited on the hole-transporting layer 4 at a deposition rate of 3.6 nm/min to a thickness of about 30 nm. On the emitting layer 5, the compound of Invention Example 1 (Compound 27) was deposited as the hole-blocking layer-cum-electron-transporting layer 6 and 7 at a deposition rate of 3.6 nm/min to a thickness of about 20 nm. On the hole-blocking layer-cum-electron-transporting layer 6 and 7, lithium fluoride was deposited as the electron-injecting layer 8 at a deposition rate of 0.36 nm/min to a thickness of about 0.5 nm. Finally, aluminum was deposited to a thickness of about 200 nm to form the cathode 9. Thus prepared device was stored in a vacuum desiccator and its characteristic properties were measured in the atmosphere at ordinary temperature.

The results of measuring the luminescence properties when a current flowed at a current density of 10 mA/cm$^2$ to the organic EL device prepared by using the compound of Invention Example 1 (Compound 27) are summarized in Table 1.

Comparative Example 1

For comparison, an organic EL device was prepared and measured for its properties under the same conditions as in Example 10, except that the material of the electron-transporting layer 7 was replaced with $Alq_3$. Namely, $Alq_3$ was deposited as the hole-blocking layer-cum-electron-transporting layer 6 and 7 at a deposition rate of 3.6 nm/min to a thickness of about 20 nm. The results of measuring the luminescence properties when a current flowed at a current density of 10 mA/cm$^2$ to the prepared organic EL device are summarized in Table 1.

TABLE 1

|  |  | Voltage [V] (@ 10 mA/cm$^2$) | Luminance [cd/m$^2$] (@ 10 mA/cm$^2$) | Luminous efficiency [cd/A] (@ 10 mA/cm$^2$) | Power efficiency [lm/W] (@ 10 mA/cm$^2$) |
| --- | --- | --- | --- | --- | --- |
| Example 10 | Compound 27 | 6.30 | 436 | 4.36 | 2.17 |
| Comparative Example 1 | $Alq_3$ | 7.10 | 378 | 3.78 | 1.68 |

Emission initiation voltage also was measured. The luminescence initiation voltage in Comparative Example 1, which employed $Alq_3$, was 4.3 V, while that in Example 10 was as low as 4.0 V.

Thus, the organic EL device of the invention has an excellent luminous efficiency and also achieves a remarkable reduction in the practical driving voltage, as compared with a device employing $Alq_3$ used as a general electron-transporting material. From this, it could be found that the emission initiation voltage was also lowered.

Example 11

As in Example 10, after the glass substrate 1 on which ITO having a film thickness of 150 nm had been deposited was washed with an organic solvent, the surface thereof was then cleaned by an oxygen plasma treatment. It was mounted in a vacuum deposition machine, which was then evacuated to 0.001 Pa or lower. Subsequently, the following Compound 137 was deposited thereon as the hole-injecting layer 3 at a deposition rate of 6.0 nm/min to a thickness of about 20 nm so as to cover the transparent anode 2. The following Compound 138 was deposited as the hole-transporting layer 4 on this hole-injecting layer 3 at a deposition rate of 6.0 nm/min to a thickness of about 40 nm. On the hole-transporting layer 4, the following Compound 139 and the following Compound 140 were deposited as the emitting layer 5 to a thickness of about 30 nm by dual vapor deposition at a deposition rate resulting in a Compound 139:Compound 140 of 5:95 (Compound 139: 0.48 nm/min, Compound 140: 9.12 nm/min). On the emitting layer 5, the compound of Invention Example 1 (Compound 27) was deposited as the hole-blocking layer-cum-electron-transporting layer 6 and 7 at a deposition rate of 6.0 nm/min to a thickness of about 30 nm. On the hole-blocking layer-cum-electron-transporting layer 6 and 7, lithium fluoride was deposited as the electron-injecting layer 8 at a deposition rate of 0.6 nm/min to a thickness of about 0.5 nm. Finally, aluminum was deposited to a thickness of 150 nm to form the cathode 9. The prepared device was subjected to measurement of characteristic properties by applying a direct current voltage in the atmosphere at ambient temperature.

The results of the luminescence properties measurement when a current flowed at a current density of 10 mA/cm$^2$ through the organic EL device prepared by using the compound of Invention Example 1 (Compound 27) are summarized in Table 2.

[Chem. 137]

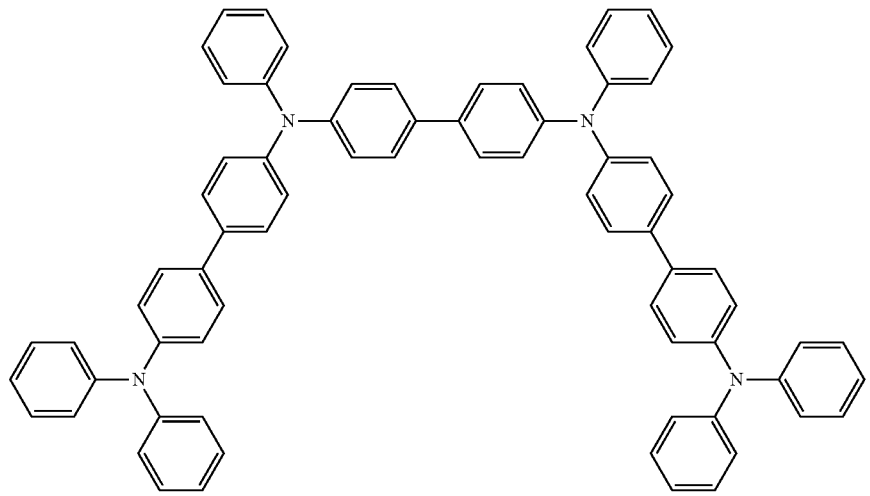

(Chemical 137)

[Chem. 138]

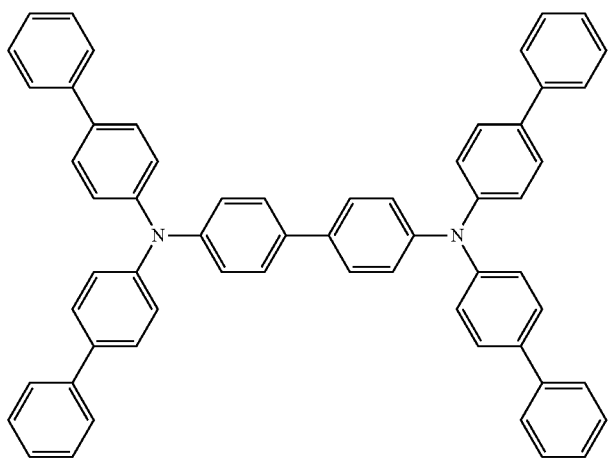

(Chemical 138)

[Chem. 139]

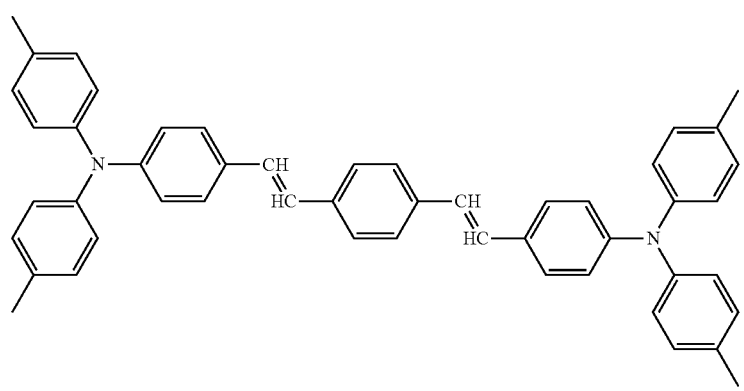

(Chemical 139)

[Chem. 140]

(Chemical 140)

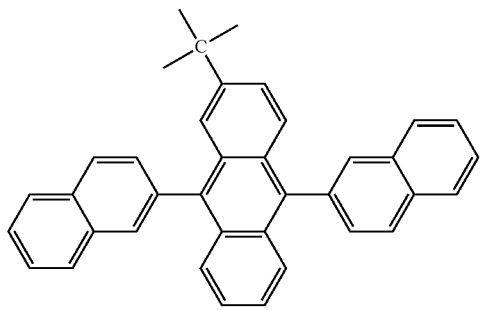

Example 12

An organic EL device was produced in the same manner as in Example 11, except that the compound of Invention Example 2 (Compound 131) was used as the hole-blocking layer-cum-the electron-transporting layer 6 and 7. The results of the luminescence properties measurements when a current flowed at a current density of 10 mA/cm² through the prepared organic EL device are summarized in Table 2.

Example 13

An organic EL device was produced in the same manner as in Example 11, except that the compound of Invention Example 3 (Compound 132) was used as the hole-blocking layer-cum-the electron-transporting layer 6 and 7. The results of the luminescence properties measurements when a current flowed at a current density of 10 mA/cm² through the prepared organic EL device are summarized in Table 2.

Example 14

An organic EL device was produced in the same manner as in Example 11, except that the compound of Invention Example 4 (Compound 133) was used as the hole-blocking layer-cum-the electron-transporting layer 6 and 7. The results of the luminescence properties measurements when a current flowed at a current density of 10 mA/cm² through the prepared organic EL device are summarized in Table 2.

Example 15

An organic EL device was produced in the same manner as in Example 11, except that the compound of Invention Example 5 (Compound 134) was used as the hole-blocking layer-cum-the electron-transporting layer 6 and 7. The results of the luminescence properties measurements when a current flowed at a current density of 10 mA/cm² through the prepared organic EL device are summarized in Table 2.

Example 16

An organic EL device was produced in the same manner as in Example 11, except that the compound of Invention Example 6 (Compound 135) was used as the hole-blocking layer-cum-the electron-transporting layer 6 and 7. The results of the luminescence properties measurements when a current flowed at a current density of 10 mA/cm² through the prepared organic EL device are summarized in Table 2.

Example 17

An organic EL device was produced in the same manner as in Example 11, except that the compound of Invention Example 7 (Compound 136) was used as the hole-blocking layer-cum-the electron-transporting layer 6 and 7. The results of the luminescence properties measurements when a current flowed at a current density of 10 mA/cm² through the prepared organic EL device are summarized in Table 2.

Comparative Example 2

For comparison, an organic EL device was prepared and measured for its properties under the same conditions as in Example 11, except that the material of the electron-transporting layer 7 was replaced with $Alq_3$. Namely, $Alq_3$ was deposited as the hole-blocking layer-cum-the electron-transporting layer 6 and 7 at a deposition rate of 6.0 nm/min to a thickness of about 30 nm. The results of the measurements are summarized in Table 2.

TABLE 2

| | | Voltage [V] (@ 10 mA/cm²) | Luminance [cd/m²] (@ 10 mA/cm²) | Luminous efficiency [cd/A] (@ 10 mA/cm²) | Power efficiency [lm/W] (@ 10 mA/cm²) |
|---|---|---|---|---|---|
| Example 11 | Compound 27 | 3.83 | 1059 | 10.58 | 8.70 |
| Example 12 | Compound 131 | 4.26 | 997 | 9.98 | 7.36 |
| Example 13 | Compound 132 | 4.69 | 968 | 9.68 | 6.49 |
| Example 14 | Compound 133 | 4.00 | 1075 | 10.75 | 8.44 |
| Example 15 | Compound 134 | 3.97 | 1030 | 10.20 | 8.10 |
| Example 16 | Compound 135 | 4.17 | 1189 | 11.89 | 8.96 |
| Example 17 | Compound 136 | 4.45 | 1180 | 11.80 | 8.33 |

TABLE 2-continued

| | | Voltage [V] (@ 10 mA/cm$^2$) | Luminance [cd/m$^2$] (@ 10 mA/cm$^2$) | Luminous efficiency [cd/A] (@ 10 mA/cm$^2$) | Power efficiency [lm/W] (@ 10 mA/cm$^2$) |
|---|---|---|---|---|---|
| Comparative Example 2 | Alq$_3$ | 5.80 | 820 | 8.25 | 4.40 |

As shown in Table 2, the driving voltages when a current flowed at a current density of 10 mA/cm$^2$ were all low with the compounds of the invention as compared with 5.80 V of Alq$_3$. Furthermore, all of the luminance, the luminous efficiency, and the power efficiency, when a current flowed at a current density of 10 mA/cm$^2$, were greatly improved.

As shown above, it could be found that the organic EL device of the invention has an excellent luminous efficiency and a power efficiency, and also achieves a remarkable reduction in the practical driving voltage as compared with a devices using Alq$_3$ used as a general electron-transporting material.

While the invention has been described in detail and with reference to specific embodiments thereof, it will be apparent to one skilled in the art that various changes and modifications can be made therein without departing from the spirit and scope thereof.

This application is based on Japanese Patent Application No. 2008-032672 which was filed on Feb. 14, 2008, and the contents thereof are incorporated herein by reference.

INDUSTRIAL APPLICABILITY

Since the compound having a pyridoindole ring structure bonded with a substituted pyridyl group according to the invention exhibits a good electron-injection property and an excellent hole-blocking ability, and is stable in a thin-film state, it is excellent as a compound for use in organic EL devices. By producing an organic EL device using the compound, high efficiencies can be obtained and a reduction in driving voltage and an improvement in durability can be attained. It becomes possible to spread the compound onto applications of, for example, electric home appliances and illuminations.

The invention claimed is:

1. A compound having a pyridoindole ring structure bonded with a substituted pyridyl group, which is represented by the following general formula (1):

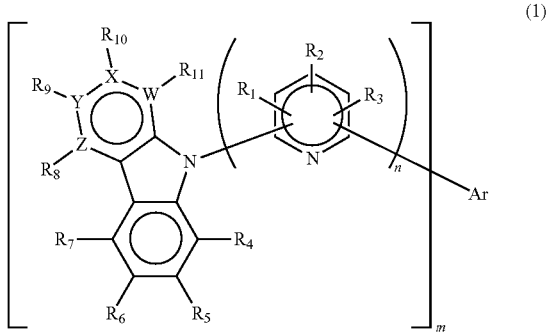

(1)

wherein Ar represents a substituted or unsubstituted aromatic hydrocarbon group, a substituted or unsubstituted aromatic heterocyclic group, or a substituted or unsubstituted condensed polycyclic aromatic group; $R_1$ to $R_3$ may be the same or different and represent a hydrogen atom, a substituted or unsubstituted aromatic heterocyclic group, or a substituted or unsubstituted condensed polycyclic aromatic group; $R_4$ to $R_{11}$ may be the same or different and represent a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, a substituted or unsubstituted aromatic heterocyclic group, or a substituted or unsubstituted condensed polycyclic aromatic group; m is an integer of 1 to 3 and n is an integer of 2 or 3; wherein one of W, X, Y or Z is a nitrogen atom; and W, X, Y, and Z represent a carbon atom or a nitrogen atom, provided that the case where $R_1$ to $R_3$ in the molecule are simultaneously all hydrogen atoms is excluded, and the nitrogen atom does not have the substituent of $R_8$ to $R_{11}$.

2. The compound having a pyridoindole ring structure according to claim 1, wherein m is 1 and n is 2 in the general formula (1).

3. The compound having a pyridoindole ring structure according to claim 1, wherein m is 1 and n is 3 in the general formula (1).

4. An organic electroluminescent device comprising a pair of electrodes and at least one organic layer interposed between the electrodes, wherein the at least one organic layer contains the compound having a pyridoindole ring structure according to claim 1.

5. The organic electroluminescent device according to claim 4, wherein m is 1 and n is 2 in the general formula (1).

6. The organic electroluminescent device according to claim 4, wherein m is 1 and n is 3 in the general formula (1).

7. The organic electroluminescent device according to claim 4, wherein the at least one organic layer comprises an electron-transporting layer, and the compound represented by the general formula (1) is present in the electron-transporting layer.

8. The organic electroluminescent device according to claim 4, wherein the at least one organic layer comprises a hole-blocking layer, and the compound represented by the general formula (1) is present in the hole-blocking layer.

9. The organic electroluminescent device according to claim 4, wherein the at least one organic layer comprises an emitting layer, and the compound represented by the general formula (1) is present in the emitting layer.

10. The organic electroluminescent device according to claim 4, wherein the at least one organic layer comprises an electron-injecting layer, and the compound represented by the general formula (1) is present in the electron-injecting layer.

11. The compound according to claim 1, wherein W is a nitrogen atom.

12. The compound according to claim 1, wherein X is a nitrogen atom.

13. The compound according to claim 1, wherein Y is a nitrogen atom.

14. The compound according to claim 1, wherein Z is a nitrogen atom.

\* \* \* \* \*